United States Patent
Downey et al.

(10) Patent No.: US 11,712,505 B2
(45) Date of Patent: Aug. 1, 2023

(54) SYSTEMS AND METHODS FOR IMPROVING CONTROL RESPONSIVENESS DURING ASPIRATION

(71) Applicant: Stryker Corporation, Kalamazoo, MI (US)

(72) Inventors: Adam Darwin Downey, Kalamazoo, MI (US); Brett Merkel, Portage, MI (US); Michael Teasdale Smith, Seattle, WA (US); Robert Mitchell Baldwin, Grand Rapids, MI (US); Benjamin Fineout, Zeeland, MI (US); Jon Bodnar, Keller, TX (US); Darryl D. Daniel, II, Pflugerville, TX (US); Anthony Gatica, Cedar Park, TX (US); Mark Friedman, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 225 days.

(21) Appl. No.: 17/279,008

(22) PCT Filed: Sep. 24, 2019

(86) PCT No.: PCT/US2019/052689
§ 371 (c)(1),
(2) Date: Mar. 23, 2021

(87) PCT Pub. No.: WO2020/068823
PCT Pub. Date: Apr. 2, 2020

(65) Prior Publication Data
US 2022/0031930 A1 Feb. 3, 2022

Related U.S. Application Data

(60) Provisional application No. 62/847,545, filed on May 14, 2019, provisional application No. 62/835,224, (Continued)

(51) Int. Cl.
*A61M 1/00* (2006.01)
*A61M 39/22* (2006.01)
(Continued)

(52) U.S. Cl.
CPC .............. *A61M 1/742* (2021.05); *A61M 1/72* (2021.05); *A61M 1/73* (2021.05); *A61M 1/743* (2021.05);
(Continued)

(58) Field of Classification Search
CPC ........... A61M 1/72; A61M 1/73; A61M 1/74; A61M 1/77; A61M 1/0023; A61M 1/0058; A61M 3/0283
See application file for complete search history.

(56) References Cited

U.S. PATENT DOCUMENTS 5,897,524 A 4/1999 Wortrich et al.
5,904,669 A * 5/1999 Schildgen ............... A61M 1/74
604/246

(Continued)

FOREIGN PATENT DOCUMENTS

CN 105407843 A * 3/2016 ............. A61F 9/007
JP 3877873 B2 * 2/2007
TW 201341003 A * 10/2013 ......... A61F 9/00736

OTHER PUBLICATIONS

International Search Report for Application No. PCT/US2019/052689 dated Jan. 21, 2020, 2 pages.
(Continued)

*Primary Examiner* — Susan S Su
*Assistant Examiner* — Ted Yang
(74) *Attorney, Agent, or Firm* — Howard & Howard Attorneys PLLC

(57) ABSTRACT

An aspiration system to control vacuum pressure in an ultrasonic surgical handpiece to result in improved control
(Continued)

responsiveness during aspiration. The system comprises a console including a vacuum pump. The system includes a cassette comprising a joint that divides a vacuum path into at least two flow paths. A first joint port couples to a first flow path. A second flow path is coupled to a second joint port, a third flow path is coupled to a third joint port, and a fourth flow path is coupled to a port on a surgical waste receiver. A first sensor senses pressure in the fourth flow path and provides a waste receiver pressure signal. A second sensor senses pressure in the third flow path and provides a tip pressure signal. The controller controls a position of a first vent valve and a second vent valve based on the waste receiver pressure signal and the tip pressure signal, respectively.

18 Claims, 16 Drawing Sheets

Related U.S. Application Data filed on Apr. 17, 2019, provisional application No. 62/749,355, filed on Oct. 23, 2018, provisional application No. 62/735,485, filed on Sep. 24, 2018.

(51) Int. Cl.
*A61M 39/24* (2006.01)
*A61M 39/28* (2006.01)

(52) U.S. Cl.
CPC .......... *A61M 1/782* (2021.05); *A61M 39/223* (2013.01); *A61M 39/24* (2013.01); *A61M 39/28* (2013.01); *A61M 2039/248* (2013.01); *A61M 2205/3331* (2013.01); *A61M 2205/50* (2013.01); *A61M 2205/52* (2013.01)

(56) References Cited

U.S. PATENT DOCUMENTS

| | | | |
|---|---|---|---|
| 6,258,111 B1 * | 7/2001 | Ross | A61F 9/00763 606/171 |
| 6,599,271 B1 * | 7/2003 | Easley | A61M 1/79 604/323 |
| 6,632,214 B2 | 10/2003 | Morgan et al. | |
| 6,908,472 B2 | 6/2005 | Wiener et al. | |
| 7,806,865 B1 * | 10/2010 | Wilson | A61M 3/0216 604/131 |
| 7,811,255 B2 | 10/2010 | Boukhny et al. | |
| 8,328,738 B2 | 12/2012 | Frankhouser et al. | |
| 8,425,452 B2 | 4/2013 | Claus et al. | |
| 8,523,812 B2 | 9/2013 | Boukhny et al. | |
| 8,617,106 B2 | 12/2013 | Zacharias | |
| 8,974,412 B2 | 3/2015 | Boukhny et al. | |
| 9,198,798 B2 | 12/2015 | Claus et al. | |
| 9,545,334 B2 | 1/2017 | Steen et al. | |
| 9,561,321 B2 | 2/2017 | Sorensen et al. | |
| 2010/0094199 A1 * | 4/2010 | Steen | A61F 9/00736 604/22 |
| 2010/0185150 A1 | 7/2010 | Zacharias | |
| 2014/0114236 A1 * | 4/2014 | Gordon | A61M 1/73 604/28 |
| 2014/0114237 A1 * | 4/2014 | Gordon | A61M 3/0216 604/257 |
| 2017/0042733 A1 | 2/2017 | Sorensen et al. | |
| 2018/0028359 A1 * | 2/2018 | Gordon | A61M 1/732 |

OTHER PUBLICATIONS

Youtube, "CUSA Clarity System Setup Video", https://www.youtube.com/watch?v=M5aCRYmCQYA, Mar. 3, 2017, 3 pages.

* cited by examiner

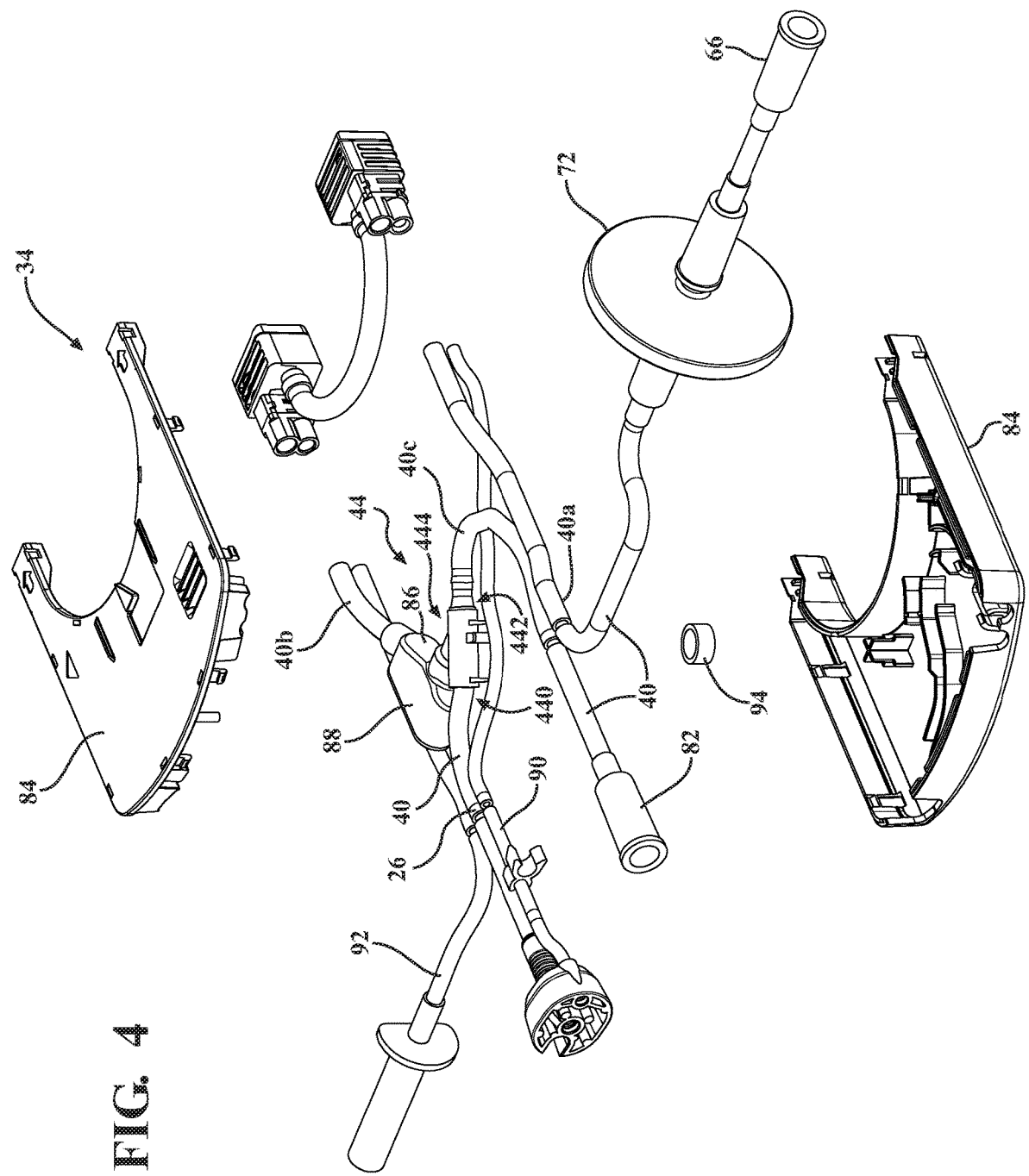

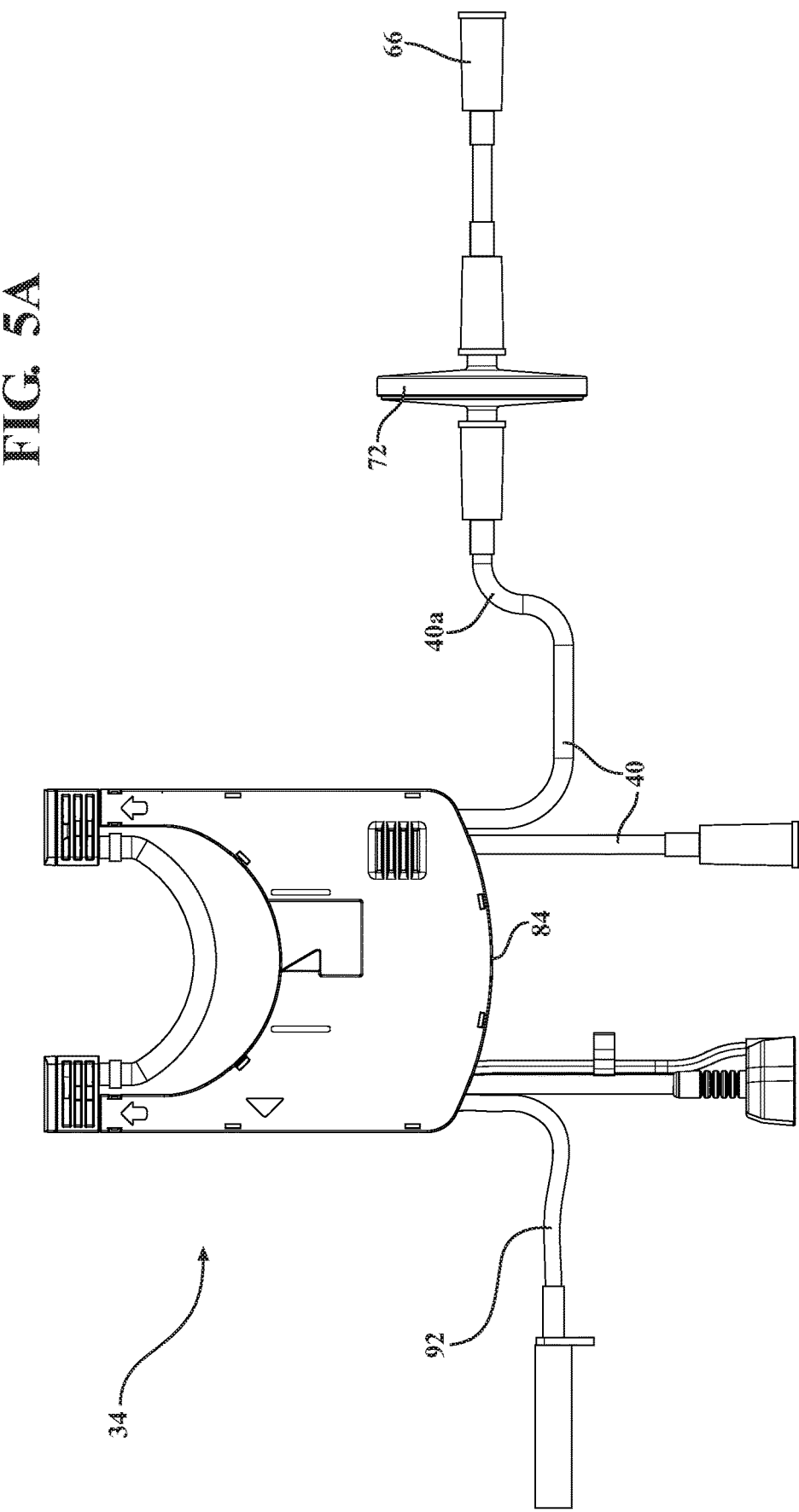

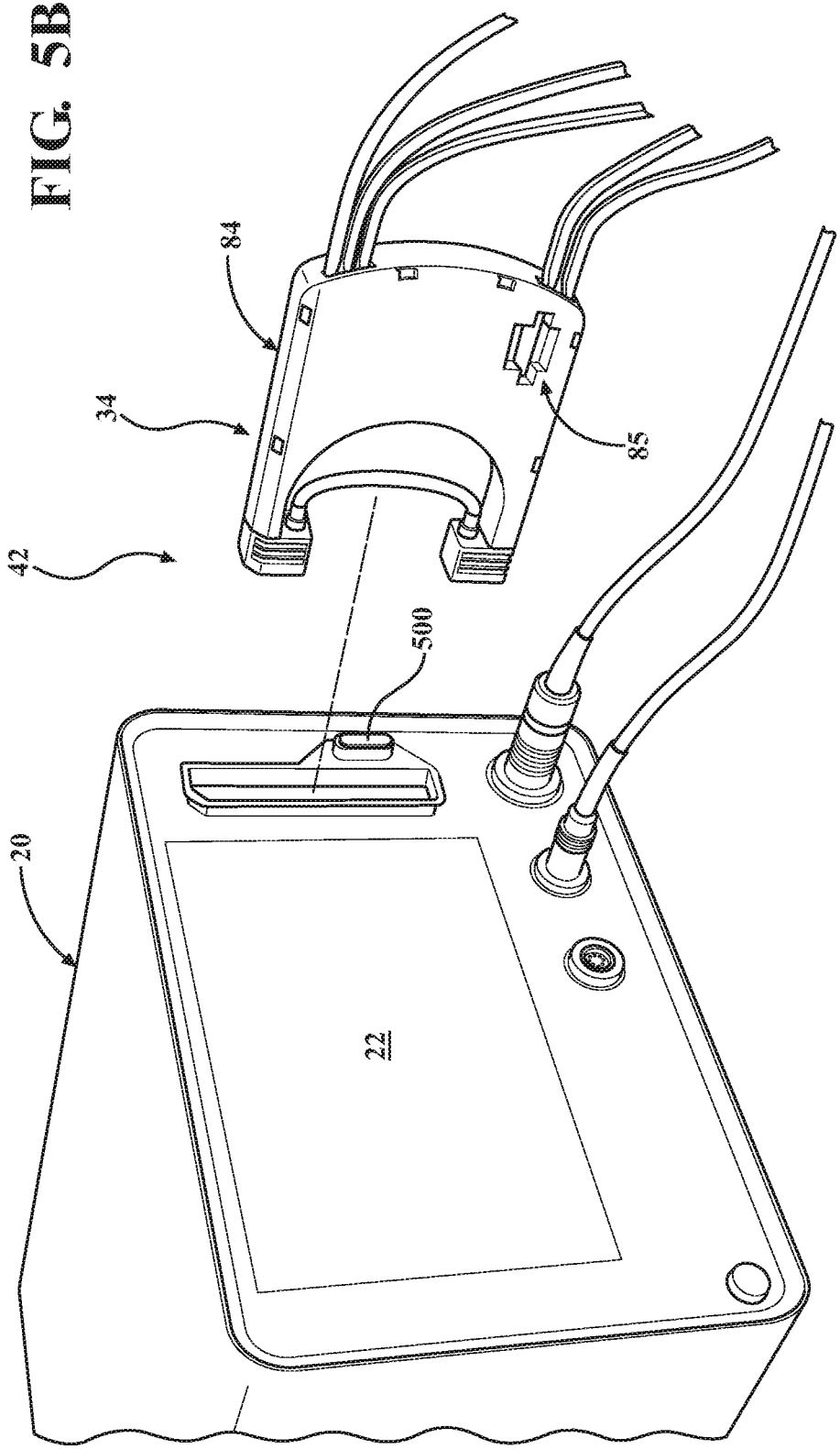

SYSTEMS AND METHODS FOR IMPROVING CONTROL RESPONSIVENESS DURING ASPIRATION

CROSS-REFERENCE TO RELATED APPLICATIONS

This application is a national stage entry of PCT Application No. PCT/US2019/052689 filed on Sep. 24, 2019, which claims priority to U.S. Provisional Application No. 62/735,485 filed on Sep. 24, 2018, U.S. Provisional Application No. 62/749,355 filed on Oct. 23, 2018, U.S. Provisional Application No. 62/835,224 filed on Apr. 17, 2019, and U.S. Provisional Application No. 62/847,545 filed on May 14, 2019, all of which are hereby incorporated herein by reference in their entirety.

BACKGROUND

The present disclosure relates, generally, to aspiration systems and methods for use with an ultrasonic surgical handpiece.

SUMMARY

An aspect of the present disclosure is to provide an aspiration system to control vacuum pressure in an ultrasonic surgical handpiece. The system comprises a vacuum pump and a surgical handpiece connector. The system has a vacuum path that extends at least partially between the surgical handpiece connector and the vacuum pump. The vacuum path includes a first connector, a second connector, and a joint between the surgical handpiece connector and the first connector. The joint divides the vacuum path into at least two lines. A first sensor is coupled to a first portion of the vacuum path, the first portion of the vacuum path positioned between the second connector and the vacuum pump. The first sensor is configured to monitor a waste receiver pressure and provide a waste receiver pressure signal. A first vent valve is coupled to the first portion of the vacuum path. A second vent valve is coupled to a terminal end of a second portion of the vacuum path, the second portion of the vacuum path originating from the joint. A second sensor is coupled to the second portion of the vacuum path and configured to monitor the vacuum pressure associated with a tip of the ultrasonic surgical handpiece and provide a tip pressure signal. A controller is configured to control the position of the first vent valve based on the waste receiver pressure signal and control the position of the second vent valve based on the tip pressure signal.

A method for controlling a vacuum level for an ultrasonic surgical handpiece is provided. The method includes driving a vacuum pump to create a vacuum pressure within the aspiration system, including creating aspiration pressure at a surgical handpiece connector. Surgical waste is deposited through a connection in the vacuum path to a surgical waste receiver. The first sensor senses a first vacuum pressure. The first sensor is located along a first portion of the vacuum path wherein the first portion of the vacuum path extends between the waste receiver connector and the vacuum pump. A first vent valve is coupled to the first portion of the vacuum path. The method further includes generating a waste receiver pressure signal, sensing a second vacuum pressure with a second sensor located along a second portion of the vacuum path that extends between the surgical handpiece connector and a second vent valve, and generating a tip pressure signal. The method includes controlling the position of the first vent valve based on the waste receiver pressure signal and controlling the position of the second vent valve based on the tip pressure signal.

Another aspect of the present disclosure is to provide an aspiration system to control vacuum pressure in an ultrasonic surgical handpiece. The system comprises a vacuum pump and a surgical handpiece connector. The system has a vacuum path that extends at least partially between the surgical handpiece connector and the vacuum pump. The vacuum path further including a first connector and a second connector for a surgical waste receiver. A joint is provided between the surgical handpiece connector and the first connector. The joint divides the vacuum path into at least two flow paths. A first vent valve is coupled to a first portion of the vacuum path wherein the first portion of the vacuum path is positioned between the waste receiver connector and the vacuum pump. A second vent valve is coupled to a terminal end of a second portion of the vacuum path, where the second portion of the vacuum path originates from the joint. A controller is provided to be configured to control the position of the first vent valve and the position of the second vent valve to maintain a pressure differential such that the pressure in the first portion of the vacuum path is higher than the pressure in the second portion of the vacuum path.

Yet another aspect of the present disclosure is to provide an aspiration system to control vacuum pressure in an ultrasonic surgical handpiece. The system comprises a vacuum pump. A vacuum path extends at least partially between the ultrasonic surgical handpiece and the vacuum pump. The vacuum path further includes a first connector, a second connector, and a joint between a surgical handpiece connector port configured to be placed in fluid communication with the ultrasonic surgical handpiece and the second connector. The joint divides the vacuum path into at least two lines. A first vent valve is coupled to a first portion of the vacuum path wherein the first portion is positioned between the first connector and the vacuum pump. A second vent valve is coupled to a terminal end of a second portion of the vacuum path wherein the second portion originates from the joint and extends along the vacuum path to the second vent valve. The system further comprises a first sensor, a second sensor, and a controller configured to determine a first flow rate based on a first input signal received from the first sensor and a second flow rate based on a second input signal received from the second sensor. The controller is further configured to output a tip clog signal based on the first flow rate and the second flow rate and control the vacuum pump based on the tip clog signal.

Yet another method of controlling vacuum pressure in an ultrasonic surgical handpiece is provided. The method includes driving a vacuum pump to create a vacuum pressure within an aspiration system. A first sensor is coupled to a first portion of a vacuum path wherein the first portion is positioned between a first connector and the vacuum pump. A first vent valve is coupled to the first portion of the vacuum path. The first sensor senses a first vacuum pressure. A second sensor is coupled to a second portion of the vacuum path, wherein the second portion originates from a joint. The joint divides the vacuum path into at least two lines and extends along the vacuum path to a second vent valve. The second sensor senses a second vacuum pressure. The method further includes generating a first input signal received from the first sensor and a second input signal received from the second sensor. Based on the first input signal and the second input signal, the method includes determining a first flow rate and a second flow rate, respectively. Then, based on the first flow rate and the second flow rate, the method includes outputting a tip clog signal and controlling the vacuum pump based on the tip clog signal.

Another aspect of the present disclosure is to provide an aspiration system comprising an ultrasonic surgical handpiece, a vacuum pump, a vacuum path that extends at least partially between the ultrasonic surgical handpiece and the vacuum pump. A first connector, a second connector, and a joint between a surgical handpiece connector port and the first connector is provided. The joint divides the vacuum path into at least two lines. A first vent valve is coupled to a first portion of the vacuum path. The first portion is positioned between the first connector and the vacuum pump. A second vent valve is coupled to a terminal end of a second portion of the vacuum path wherein the second portion originates from the joint and extends along the vacuum path to the second vent valve. A first sensor is coupled to the first portion of the vacuum path and a second sensor is coupled to the second portion of the vacuum path is also provided. The system also includes a controller configured to: determine a first flow rate based on a first input signal received from the first sensor, determine a second flow rate based on a second input signal received from the second sensor, output a tip clog signal based on the first flow rate and the second flow rate, and control the vacuum pump based on the tip clog signal.

Yet another aspect of the present disclosure is to provide an aspiration system to control vacuum pressure in an ultrasonic surgical handpiece to result in improved control responsiveness during aspiration. The aspiration system comprises a console including a vacuum pump, a surgical waste receiver with a first surgical waste receiver port and a second surgical waste receiver port, a joint defining a first joint port, a second joint port, and a third joint port. The first joint port couples to a first flow path that extends from the ultrasonic surgical handpiece. A second flow path is coupled to the second joint port and the first surgical waste receiver port. A third flow path is coupled to the third joint port. A fourth flow path is coupled to the second surgical waste receiver port. A first sensor is positioned to sense pressure in the fourth flow path and configured to monitor a waste receiver pressure and provide a waste receiver pressure signal. A second sensor is positioned to sense pressure in the third flow path and configured to monitor a vacuum pressure associated with the tip of the ultrasonic surgical handpiece and provide a tip pressure signal. A first vent is coupled to the fourth flow path. A second vent is coupled to the third flow path. The system also includes a controller configured to control a position of the first vent valve based on the waste receiver pressure signal and control a position of the second vent valve based on the tip pressure signal. The vacuum pump is coupled to the fourth flow path.

Another method of controlling an aspiration system to result in improved control responsiveness during operation is provided. The aspiration system includes a vacuum pump, an ultrasonic surgical handpiece, a surgical waste receiver, a clean side flow path, and a dirty side flow path. The system also includes a fluid backflow device in communication with the clean side flow path, and a clean side venting mechanism in communication with the dirty side flow path. The clean side flow path positioned between the vacuum pump and the surgical waste receiver and the dirty side flow path positioned between the ultrasonic surgical handpiece and a fluid backflow device. The method comprises sensing a first pressure within the dirty side flow path, sensing a second pressure within the clean side flow path, controlling the fluid backflow device based on the first pressure, and controlling the clean side venting mechanism based on the second pressure.

Yet another aspect of the present disclosure is to provide an aspiration system to control vacuum pressure in an ultrasonic surgical handpiece to result in improved control responsiveness during aspiration. The system includes a console comprising a vacuum pump, an ultrasonic surgical handpiece, a surgical waste receiver, a clean side flow path, and a dirty side flow path. The clean side flow path is positioned between the vacuum pump and the surgical waste receiver. A fluid backflow device is provided and in communication with the clean side flow path and a clean side venting mechanism is in communication with the dirty side flow path. The dirty side flow path is positioned between the ultrasonic surgical handpiece and the fluid backflow device.

Yet another aspect of the present disclosure is to provide an aspiration system to control vacuum pressure in an ultrasonic surgical handpiece to result in improved control responsiveness during aspiration. The system includes a console for being fluidly coupled to the ultrasonic surgical handpiece wherein the console comprises a controller, a vacuum pump, a first sensor, a fluid backflow device, a second sensor, and a clean side venting mechanism. The controller is configured to control the clean side venting mechanism based on an input signal from the first sensor and control the fluid backflow device based on an input signal from the second sensor.

Yet another aspect of the present disclosure is to provide an aspiration system to control vacuum pressure in an ultrasonic surgical handpiece to result in improved responsiveness during aspiration. The system includes a console for being fluidly coupled to the ultrasonic surgical handpiece wherein the console comprises a controller, a vacuum pump, a first venting mechanism, and a second venting mechanism, said system configured to be placed in communication with a surgical waste receiver. The controller is configured to control the first venting mechanism in response to aspiration of liquid and solid material through the surgical handpiece and the controller is configured to control the second venting mechanism to maintain a desired pressure in the surgical waste receiver.

BRIEF DESCRIPTION OF THE DRAWINGS

Referring now to the drawings, exemplary illustrations are shown in detail. Although the drawings represent schematic embodiments, the drawings are not necessarily to scale and certain features may be exaggerated to better illustrate and explain an innovative aspect of an illustrative embodiment. Further, the exemplary illustrations described herein are not intended to be exhaustive or otherwise limiting or restricting to the precise form and configuration shown in the drawings and disclosed in the following detailed description.

Advantages of the present disclosure will be readily appreciated as the same becomes better understood by reference to the following detailed description when considered in connection with the accompanying drawings wherein:

FIG. 4 is an exploded view of a cassette including tubing for an aspiration and irrigation system.

FIG. 5A is a view of the assembled cassette, according to one example.

FIG. 5B is view of the assembled cassette being inserted into the control console, according to one example.

DETAILED DESCRIPTION

I. Overview of the System

Figure 1:
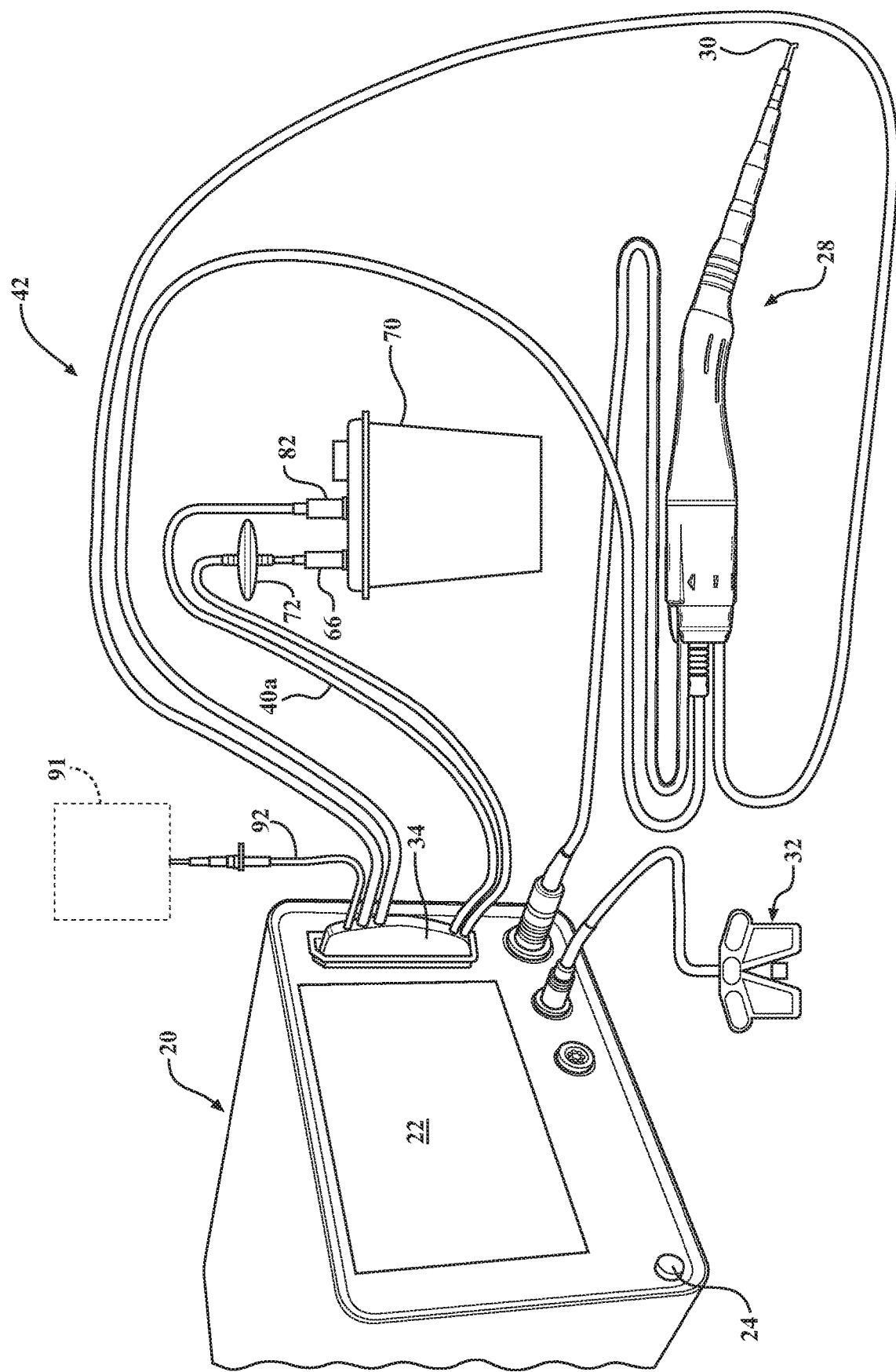
FIG. 1 depicts certain components of an aspiration system, including an ultrasonic surgical handpiece and a control console.

FIG. 1 depicts certain components of an aspiration system 42. The aspiration system 42 is described for use with an ultrasonic surgical handpiece 28 and a console 20, but could in certain configurations, be used for other handpieces that are actuated through mechanical means, such as powered burs, drills, and saws. The ultrasonic surgical handpiece 28 includes an ultrasonic surgical handpiece tip 30, through which a surgical site is aspirated. It will be appreciated that aspiration includes any form of matter from the surgical site. For example, the ultrasonic surgical handpiece 28 may aspirate liquid and solid material from the surgical site through the ultrasonic surgical handpiece. It will further be appreciated that, unless otherwise specified, "proximal" is understood to mean toward the surgical handpiece tip 30 and "distal" is understood to mean away from the surgical handpiece tip 30.

The aspiration system 42 includes the console 20 that provides power and aspiration to the ultrasonic surgical handpiece 28. The console 20 includes a display 22 to show the amount of power, irrigation, aspiration, or combination thereof. The console 20 may also be connected to a foot pedal 32, hand switch, or any other control device that controls whether the surgical handpiece tip 30 is actively vibrating when the ultrasonic surgical handpiece 28 is powered on.

The aspiration system 42, according to one configuration, includes the console 20 comprising a vacuum pump 74, a cassette 34, and the ultrasonic surgical handpiece 28. In another configuration, the aspiration system 42 includes the surgical console 20, the vacuum pump 74, a surgical waste receiver 70 or other waste receptacle, the cassette 34, and the ultrasonic surgical handpiece 28.

Figure 2:
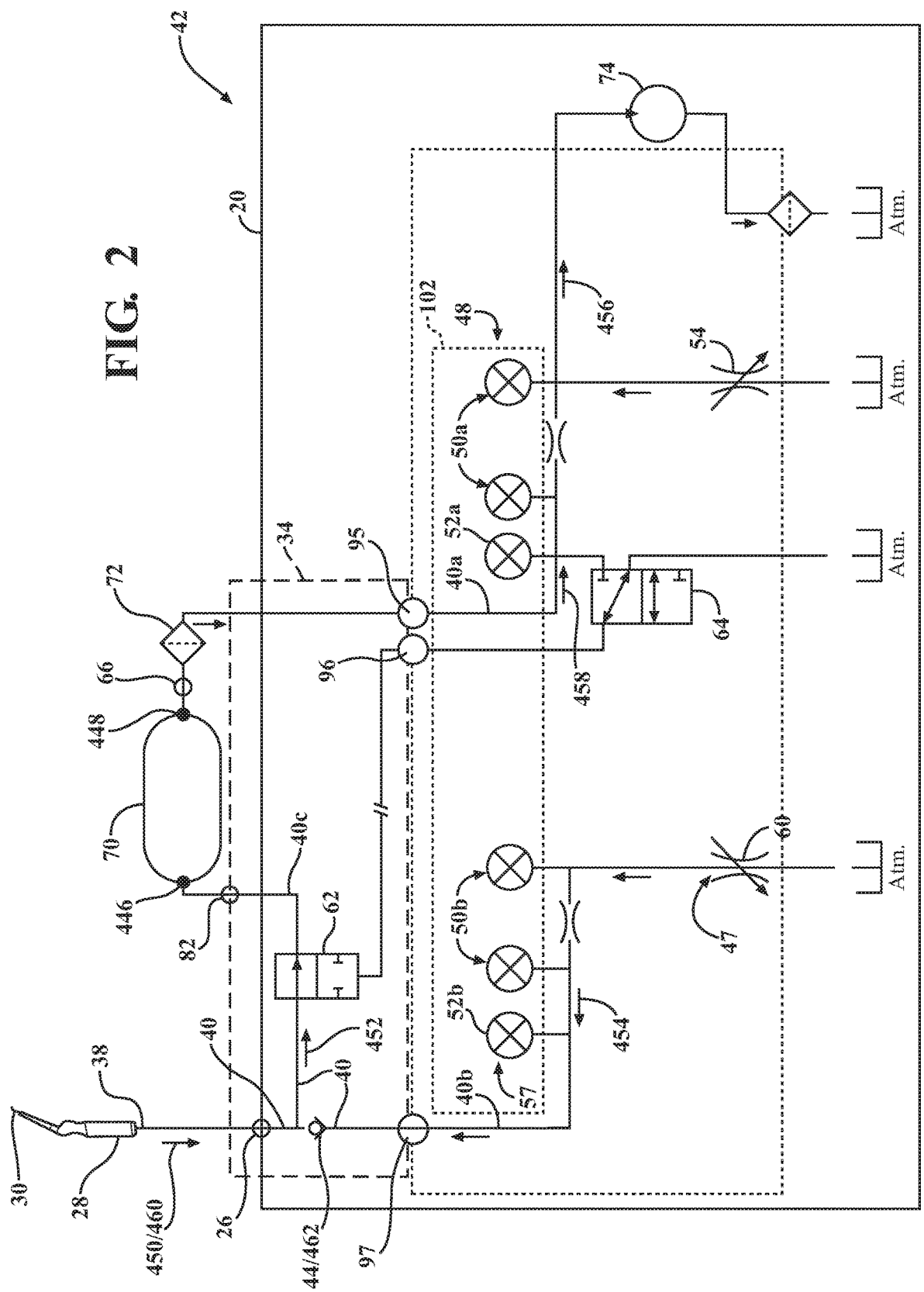
FIG. 2 is a schematic drawing of components in the aspiration system for removing irrigation fluid and surgical waste from a surgical site, according to one example.

FIG. 2 is a schematic drawing of components in the aspiration system 42 for removing irrigation fluid and surgical waste from the surgical site. The console 20, the surgical waste receiver 70, the cassette 34, and/or the ultrasonic surgical handpiece 28 may comprise any number of ports/connectors such that the components may be fluidly coupled together. For example, the ultrasonic surgical handpiece 28 may include an ultrasonic surgical handpiece connector 26. The components of the aspiration system 42 are coupled together with a variety of tubing or lines to form a vacuum path 40. The vacuum pump 74 generates vacuum pressure throughout the vacuum path 40 which causes the majority of the surgical waste and irrigation fluid, which may be in the form of a liquid, gas, solid or combination thereof, to move through the vacuum path 40, and ultimately to the surgical waste receiver 70.

The cassette 34 may include a portion of lines comprising the vacuum path 40. When the cassette 34 is inserted into the console 20, the cassette 34 and the console 20 are aligned to a first port 95, a second port 96, and a third port 98 of an aspiration manifold 36 within the console 20 such that lines of the vacuum path 40 run from the ultrasonic surgical handpiece 28, a pinch valve 62, and a filter 72 to the respective ports as shown in FIG. 2. The surgical handpiece tip 30 is coupled to a waste line 38 and the waste line 38 runs from the surgical handpiece tip 30 to a joint 44 in the cassette 34. The joint 44, as shown in FIG. 2, divides the vacuum path 40 into at least two flow paths. It will be appreciated that lines may be described as tubing and/or flow paths, unless specifically stated otherwise. The joint 44 may include a fluid backflow device 462 that allows air to pass but prevents surgical waste or aspiration fluid from entering portions of the vacuum path 40 beyond the fluid backflow device 462.

In one configuration, the joint 44 comprises a first joint port 440, a second joint port 442 and a third port joint 444. The surgical waste receiver 70 includes a first surgical waste receiver port 446 and a second surgical waste receiver port 448. A first surgical waste receiver connector 82 connects to the first surgical waste receiver port 446 and a second surgical waste receiver connector 66 connects to the second surgical waste receiver port 448.

Flow paths of the vacuum path 40 may be described relative to the joint 44, the surgical waste receiver 70, and the vacuum pump 74. The first joint port 440 is coupled to a first flow path 450 that extends from the ultrasonic surgical handpiece 28. A second flow path 452 is coupled to the second joint port 442 and to the first surgical waste receiver port 446. A third flow path 454 is coupled to the third joint port 444 and a fourth flow 456 path is coupled to the second surgical waste receiver port 448. The fourth flow path 456 extends, at least partially, from the second surgical waste receiver port 448 to the vacuum pump 74.

Alternatively described, the vacuum path 40 may be divided into three portions. A first portion 40a of the vacuum path 40 is positioned between the second surgical waste receiver connector 66 and the vacuum pump 74. A second portion 40b of the vacuum path 40 originates from the joint 44 and extends along the vacuum path 40 to a second vent valve 60. The second vent valve 60 may be used to vent the vacuum path 40 to the atmosphere as will be described further below. A third portion 40c of the vacuum path 40 extends, at least partially, from the joint 44 to the first surgical waste receiver connector 82.

It will be appreciated that the first flow path 450 is associated with the waste line 38; the second flow path 452 is associated with the third portion 40c of the vacuum path 40; the third flow path 454 is associated with the second portion 40b of the vacuum path 40; the fourth flow path 456 is associated with the first portion 40a of the vacuum path 40, unless otherwise specifically stated.

Figure 3:
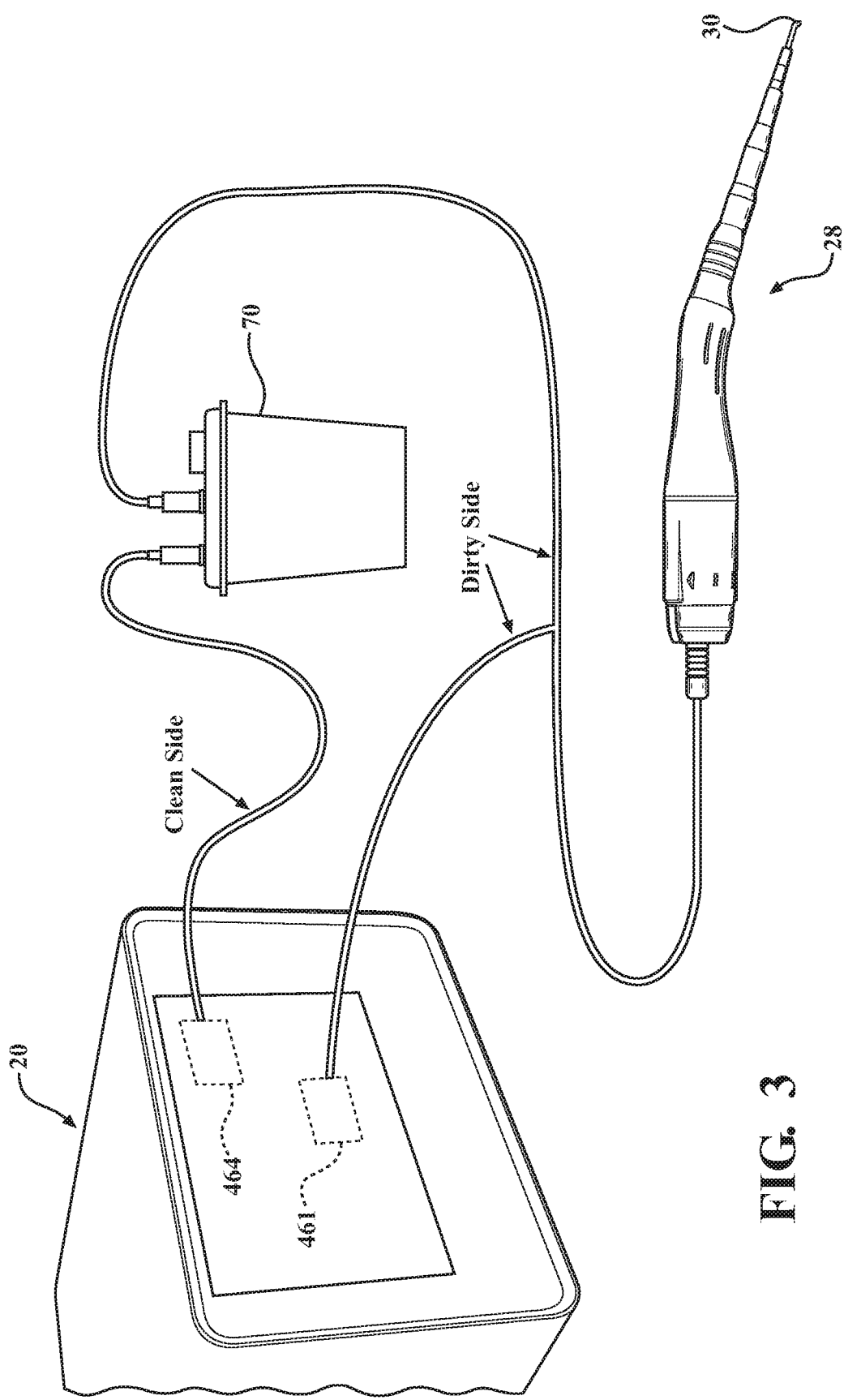
FIG. 3 depicts certain components of the aspiration system, according to one example, with a distinction between a clean side and a dirty side of a flow path.

Additionally, or alternatively, the vacuum path 40 may be divided into two flow paths: a clean side flow path 458 and a dirty side flow path 460. The clean side flow path 458 is positioned between the vacuum pump 74 and the surgical waste receiver 70. The dirty side flow path 460 is positioned between the ultrasonic surgical handpiece 28 and the fluid backflow device 462. The fluid backflow device 462 may be provided in communication with the dirty side flow path 460 and a clean side venting mechanism 464 may be provided in communication with the clean side flow path 458. It will be appreciated that the clean side venting mechanism 464 may be a first venting mechanism including a first vent valve 54. In some configurations, the system 42 comprises a second venting mechanism 461 including a second vent valve 60. The fluid backflow device 462 may be implemented to aid in dissipation of vacuum pressure by introducing fresh air to the dirty flow path 460. Referring to FIG. 3, a "clean side" is void of any surgical waste (e.g., tissue and fluid) and the "dirty side" includes surgical waste from aspiration of the surgical site. The "clean side" is between the vacuum pump 74 (not shown in FIG. 3) and the surgical waste receiver 70. The "dirty side" is between the ultrasonic surgical handpiece 28 and the fluid backflow device 462 (not shown in FIG. 3). In other words, in this configuration, the surgical waste receiver 70 may provide a functional boundary between the clean side and the dirty side of the flow path.

To allow venting directly through the second venting mechanism 461 to the third portion 40c and/or the dirty side flow path 460, the combination of the fluid backflow device 462, gravity, and the directionality of the aspiration/suction (tending to keep surgical waste flowing away from the fluid backflow device 462), the dirty side flow path 460 may be used. These design features ensure that surgical waste does not contaminate the second venting mechanism 461.

By providing a plurality of lines, paths, and/or portions of the vacuum path 40, an advantage to the system 42 is a dual regulation of pressure by a first sensor 48 and a second sensor 57. Additionally, another advantage of the system 42 is an improved control responsiveness during operation with a clog detection. The first sensor 48 is positioned to sense pressure in the first portion 40a of the vacuum path 40 and monitor a waste receiver pressure. The second sensor 57 is positioned to sense pressure in the second portion 40b of the vacuum path 40 and monitor a vacuum pressure associated with the ultrasonic surgical handpiece tip 30. The system 42 includes a controller 102 for controlling a first vent valve 54 and a second vent valve 60 based on signals from the first and second sensors 48, 57. Additionally, or alternatively, the clean side venting mechanism 464 may include the first vent valve 54. The fluid backflow device 462 may be the joint 44, including a joint valve or the ball valve 86. The first and second vent valves 54, 60 may be opened to introduce the atmosphere or fresh air into the system 42 to dissipate vacuum pressure. Dual regulation and clog detection by the first sensor 48 and the second sensor 57 will be discussed in greater detail below.

With the dual regulation, the system 42 regulates pressure in the surgical waste receiver 70 and the pressure of the surgical site. The system 42 results in improved control responsiveness during various operations of the ultrasonic surgical handpiece 28, overall wider range of suction control, finer adjustments of aspiration settings, and more optimal aspiration performance. For example, with the dual regulation (e.g., use of the first venting mechanism and the second venting mechanism), significant lower suction levels are achievable which significantly reduces tissue "tugging" force, which is important in avoiding delicate structures, thereby providing comfort to a patient and an operator.

Once liquid and solid material is aspirated from the surgical site with the ultrasonic surgical handpiece 28 and into the waste line 38, the surgical waste flows through the joint 44 and the pinch valve 62. In this configuration, the vacuum path 40 is open to the surgical waste receiver 70, and gravity removes the surgical waste from the second portion 40b of the vacuum path 40. The second surgical waste receiver connector port 448 is coupled to the second surgical waste receiver connector 66 which connects to the filter 72. The filter 72 is proximal as compared to the surgical waste receiver 70 from the console's perspective. The filter 72 is designed to remove remaining traces of surgical waste from the second portion 40b of the vacuum path 40 that were not trapped by the surgical waste receiver 70. The filter 72 may be a part of the cassette assembly and/or tubing, so that the filter 72 may be easily disposed of and replaced after an operation. The filter 72 is coupled to the console 20 through the first port 95 via another line.

FIG. 4 depicts an exploded view of the cassette 34. In one configuration, the cassette may be optional. In other words, while the cassette 34 itself may be omitted, the lines that couple the ultrasonic surgical handpiece 28 to the surgical waste receiver 70 would still be included, as well as the joint 44. As shown in FIG. 4, the joint 44 includes a ball valve 86 or any other type of fluid backflow devices 462.

The ball valve 86/fluid backflow device 462 is a one-way valve that allows air to pass from the second portion 40b of the vacuum path 40 to the third portion 40c of the vacuum path 40 but prevents surgical waste or aspiration fluid from entering the second portion 40b of the vacuum path 40 from the surgical handpiece tip 30. The ball valve 86 is installed so that the ball of the ball valve 86 is biased to the open position by gravity and may be forced upward to the closed position by impingement of liquid from the third portion 40c of the vacuum path 40. A chamber 88 is also included adjacent and distal to the ball vale 86 to hold any surgical waste that does pass the ball valve 86 into the second portion 40b of the vacuum path 40. The chamber 88 may have an angled floor. The angled floor of the chamber 88 causes any surgical waste that does pass the ball valve 86 to flow back into the third portion 40c of the vacuum path 40 once the ball of the ball valve 86 returns to its resting position. Other types of valves may be used in place of the ball valve to control the flow of fluid in the second portion 40b of the vacuum path 40.

As shown in FIGS. 4-5B, the cassette 34 may be used to more easily route the irrigation and aspiration lines relative to the console 20. Both irrigation lines 90 and 92 and the vacuum path 40 lines are included within a single cassette 34 in this configuration. In certain configurations, either irrigation lines 90/92 may be provided to couple the ultrasonic surgical handpiece 28 to an irrigation source 91. In some configurations, irrigation fluid may be routed to the ultrasonic surgical handpiece connector 26 through the cassette 34. By including both irrigation and aspiration in the same cassette 34 simplifies set-up and operation of the ultrasonic aspirator. Presetting the tubing within the cassette 34 also avoids user error that may, for example, cause misalignment of the pinch valve 62 relative to the vacuum path 40.

FIGS. 5A and 5B are views of the cassette 34. A user inserts the cassette 34 into the console 20 in a single motion requiring one hand. By completing this single action, a cassette RFID (radio frequency identification) tag 94 is detected by the console 20 indicating the cassette 34 has been fully inserted. The pinch valve 62 can be user activated once cassette 34 is inserted and aligned. The pinch valve 62, when actuated, compresses the tubing of the third portion 40c of the vacuum path 40 retained in the cassette 34.

Figure 7A:
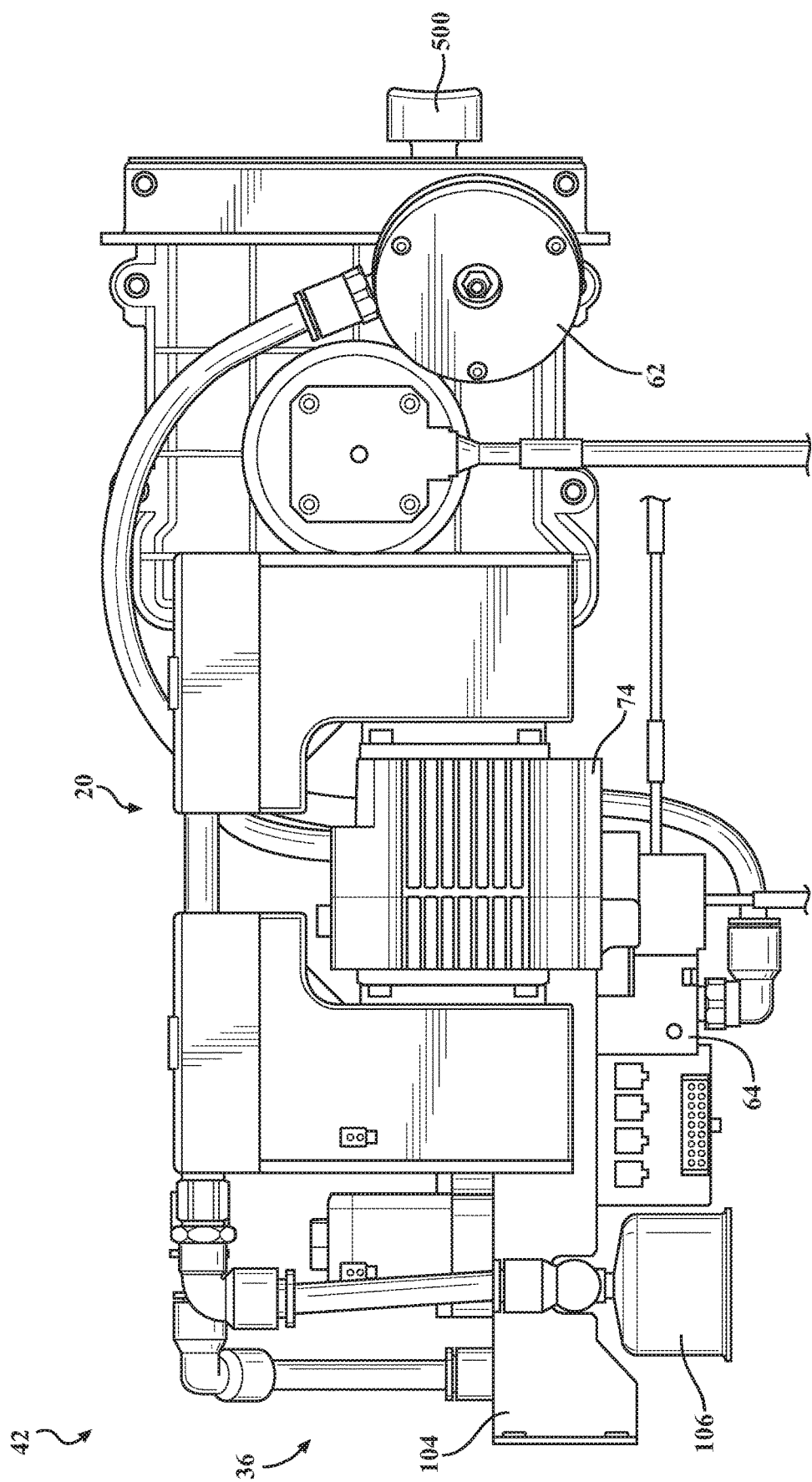
FIG. 7A is a perspective view of certain internal components of the aspiration system within the console, including the pinch valve.
Figure 7B:
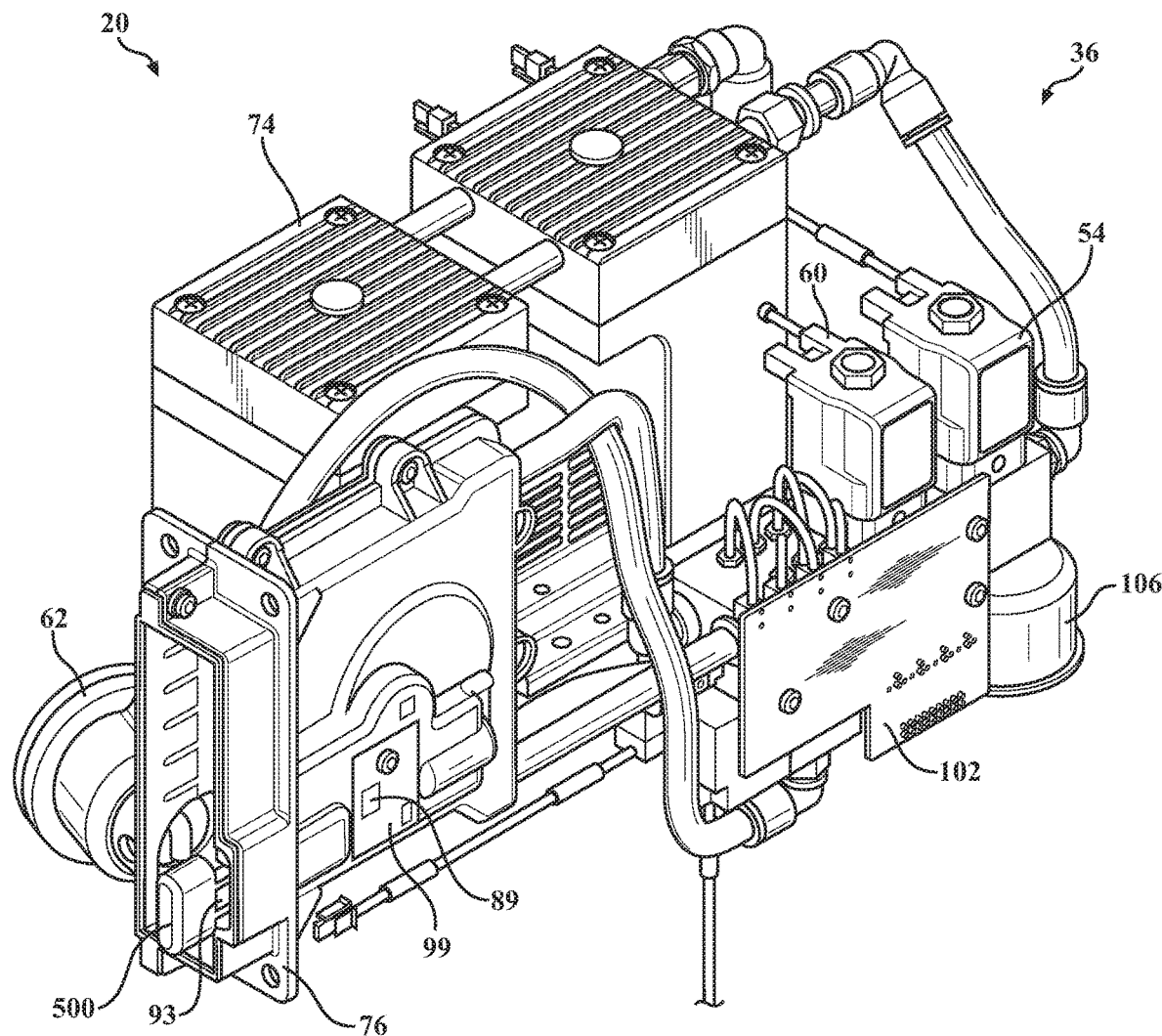
FIG. 7B is another perspective view of the internal components of the aspiration system within the console, including a controller and an aspiration manifold.

A cassette release button 500 is provided on the console 20, as shown in FIGS. 7A-7B. The cassette receptacle 76 may include one or more sensors, such as Hall effect sensors, magnetic sensors, or other suitable sensors, that generate signals in response to depression of the cassette release button 500. In this configuration, as shown in FIG. 7B, the cassette release button 500 includes a magnet 93 and the cassette receptacle 76 includes a printed circuit board assembly (PCBA) 99 including a Hall effect sensor 89. The magnet 93 aids in detection of whether the cassette 34 is inserted and/or will be ejected. As the cassette release button 500 is depressed, the magnet 93 aids in detecting when the cassette 34 is about to eject as the magnet 93 gets closer to the Hall effect sensor 89. In response, the system 42, the controller 102, and/or the PCBA 99 releases the pinch valve 62 before the cassette 34 is ejected. This ensures that the cassette 34 is properly ejected.

Figure 6:
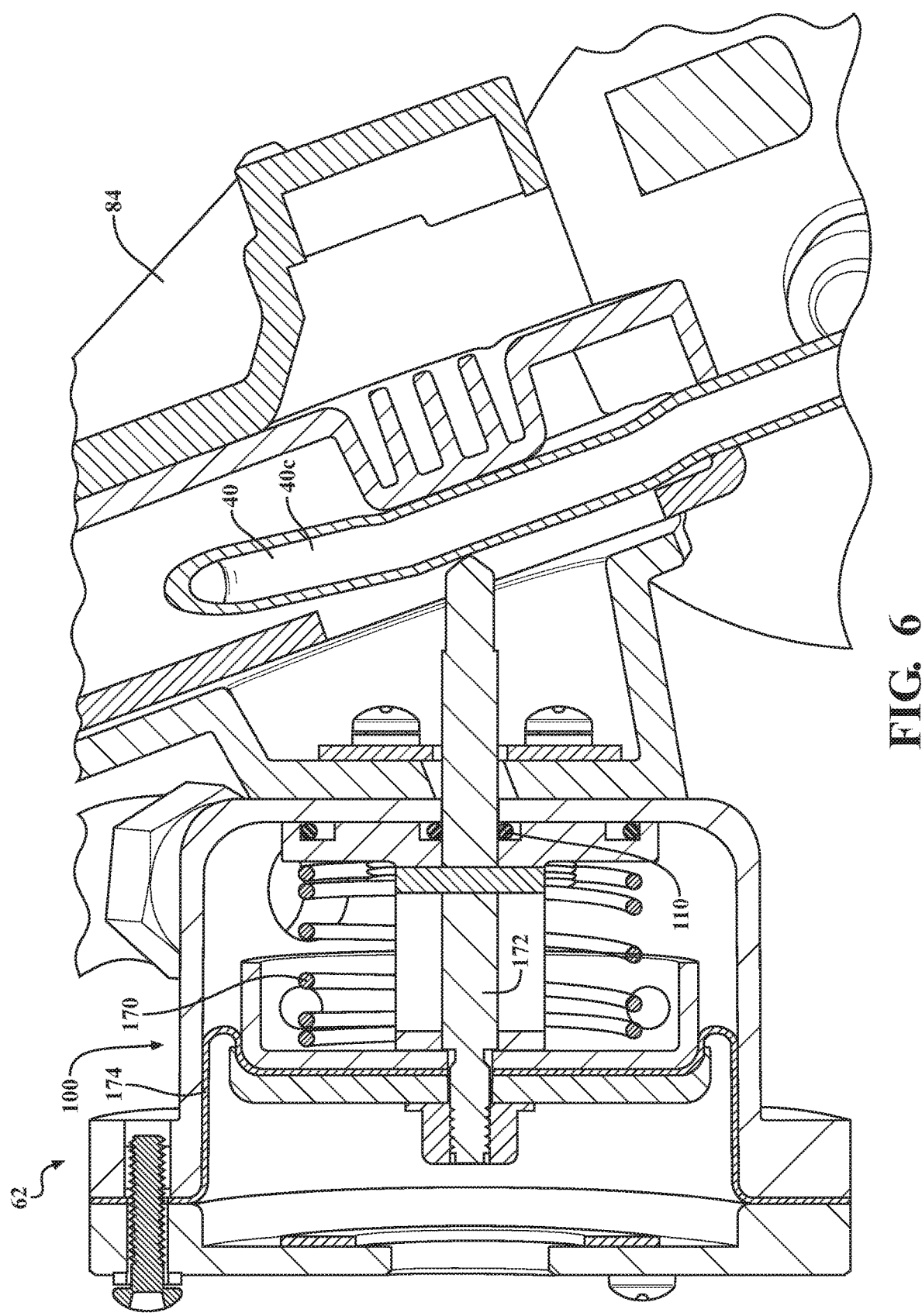
FIG. 6 depicts a cross section of a pinch valve in the console being aligned to the cassette and a portion of the vacuum path of the system.

A cassette housing 84 includes an opening 85, shown in FIG. 5B, over the tubing that defines the third portion 40c of the vacuum path 40 that aligns with the pinch valve 62. When the cassette 34 is inserted into the console 20, as shown in FIG. 5B, the opening 85 of the cassette housing 84 is positioned adjacent pinch valve 62. As shown in FIG. 6, if the pinch valve is actuated, a rod 172 is used to pinch the third portion 40c of the vacuum path 40. The pinch valve 62 prevents vacuum pressure from reaching the ultrasonic surgical handpiece tip 30. More specifically, the pinch valve 62 affects a degree of occlusion in the vacuum path 40 by ensuring a responsive cutoff of vacuum pressure at the ultrasonic surgical handpiece tip 30.

Further, the console 20 may further include the 3-way solenoid valve 64, as shown in FIG. 7A. The 3-way solenoid valve 64 controls actuation of the pinch valve 62. The 3-way solenoid valve 64 is connected to the vacuum pump 74 through the first portion 40a of the vacuum path 40. When the aspiration system 42 is operating to remove surgical waste at the surgical handpiece tip 30, the pinch valve 62 is connected to the atmosphere by the 3-way solenoid valve 64. In this configuration, the pinch valve 62 is pneumatic and is opened and closed by moving the solenoid of the 3-way solenoid valve 64 to allow vacuum pressure to engage a mechanical actuator 100, including a coil 170, the rod 172, a gasket 174, and a pump head 110, of the pinch valve 62 as shown in FIG. 6. In other configurations, the pinch valve 62 is electrically actuated, and the 3-way solenoid valve 64 is not required.

Related to the pinch valve 62 and the 3-way solenoid valve 62, the aspiration system 42 is capable of operating in one or more modes, including a Standard Mode and a Sync Mode. In Standard Mode, the pinch valve 62 and 3-way solenoid valve 64 operate in the same way whether the foot pedal 32 is depressed to run the surgical handpiece 28 or not. Whenever power to the console 20 is on, suction is provided at the ultrasonic surgical handpiece tip 30 in Standard Mode.

In Standard Mode, the pinch valve 62 is continuously in a resting state where the pinch valve 62 is openly connecting the surgical handpiece tip 30 to the surgical waste receiver 70 and vacuum pump 74 via the vacuum path 40.

Specifically, in Standard Mode, the 3-way solenoid valve 64 is always opened to the atmosphere and closed to the vacuum path 40. This allows vacuum to reach the surgical handpiece tip 30 and provide suction at the surgical site. For an aspiration system designed to be always on, the system 42 could be made without the 3-way solenoid valve 64 or pinch valve 62.

A second potential mode of operation for aspiration is Sync Mode. In Sync Mode, suction is not permitted to reach the surgical site when the foot pedal 32 is not depressed to vibrate the surgical handpiece tip 30. Specifically, pinch valve 62 is in active state, closing off the connection between the surgical handpiece tip 30 and vacuum pump 74, when the foot pedal 32 is not depressed and the ultrasonic surgical handpiece tip 30 is not vibrating. The pinch valve 62 is actuated by the 3-way solenoid valve 64. The solenoid of the 3-way solenoid valve 64 moves so that the pinch valve 62 is closed to the atmosphere and opened to the vacuum path 40 when the foot pedal 32 is not depressed. This prevents vacuum from reaching the surgical handpiece tip 30 and the surgical site. The second vent valve 60 is also opened to the atmosphere to quickly dissipate any vacuum pressure at the surgical site when the foot pedal 32 is not depressed.

In Sync Mode, the aspiration system 42 acts the same as described for Standard Mode when the foot pedal 32 is depressed to operate the ultrasonic surgical handpiece 28. For example, the pinch valve 62 is in resting state such that the vacuum path 40 is open between the ultrasonic surgical handpiece tip 30 and the vacuum pump 74 when foot pedal 32 is depressed.

The vacuum pump 74 selectively connects to the pinch valve 62 through the 3-way solenoid valve 64. The pinch valve 62 is connected to a receptacle 76 for the cassette 34, shown in FIGS. 7A-7B. In this configuration, the vacuum pump 74 uses a dual diaphragm design that keeps the vacuum pump 74 elements separated from the pumped air. In addition, two diaphragms provide twice as much airflow for every stroke of the piston as a single diaphragm, allowing the vacuum pump 74 to be operated at a low speed. Further, in this configuration, a pump head 110 may be plastic to reduce mechanical pumping noise. As shown in FIG. 5, the pump head 110 is in-line to reduce the length of the vacuum path 40. Reducing the length of tubes near the vacuum pump 74 limits the potential for tubes to vibrate and generate unwanted noise.

FIG. 7B provides a view of the aspiration manifold 36, including the first vent valve 54, the second vent valve 60, and the controller 102. FIG. 7B also shows a cassette receptacle 76 where the user inserts the cassette 34. Also visible in FIG. 7B, the receptacle 76 for the cassette 34 includes an opening to the pinch valve 62. Upon proper insertion of the cassette 34, the opening 85 in the cassette housing 84 aligns with the opening in the receptacle 76 allowing the pinch valve 62 to engage the lines of the vacuum path 40.

Figure 7C:
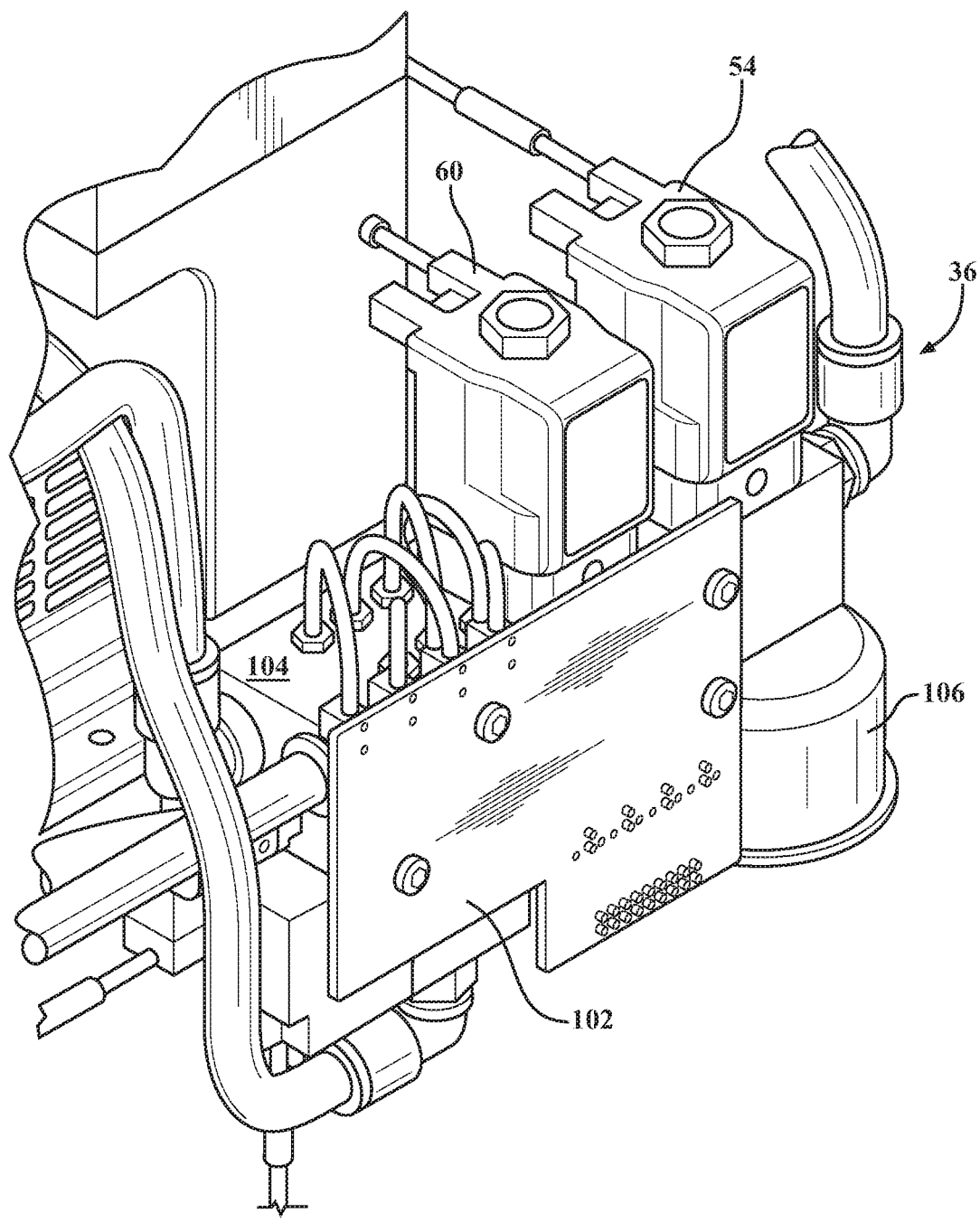
FIG. 7C is a zoomed view of the aspiration manifold of the aspiration system within the console.
Figure 8:
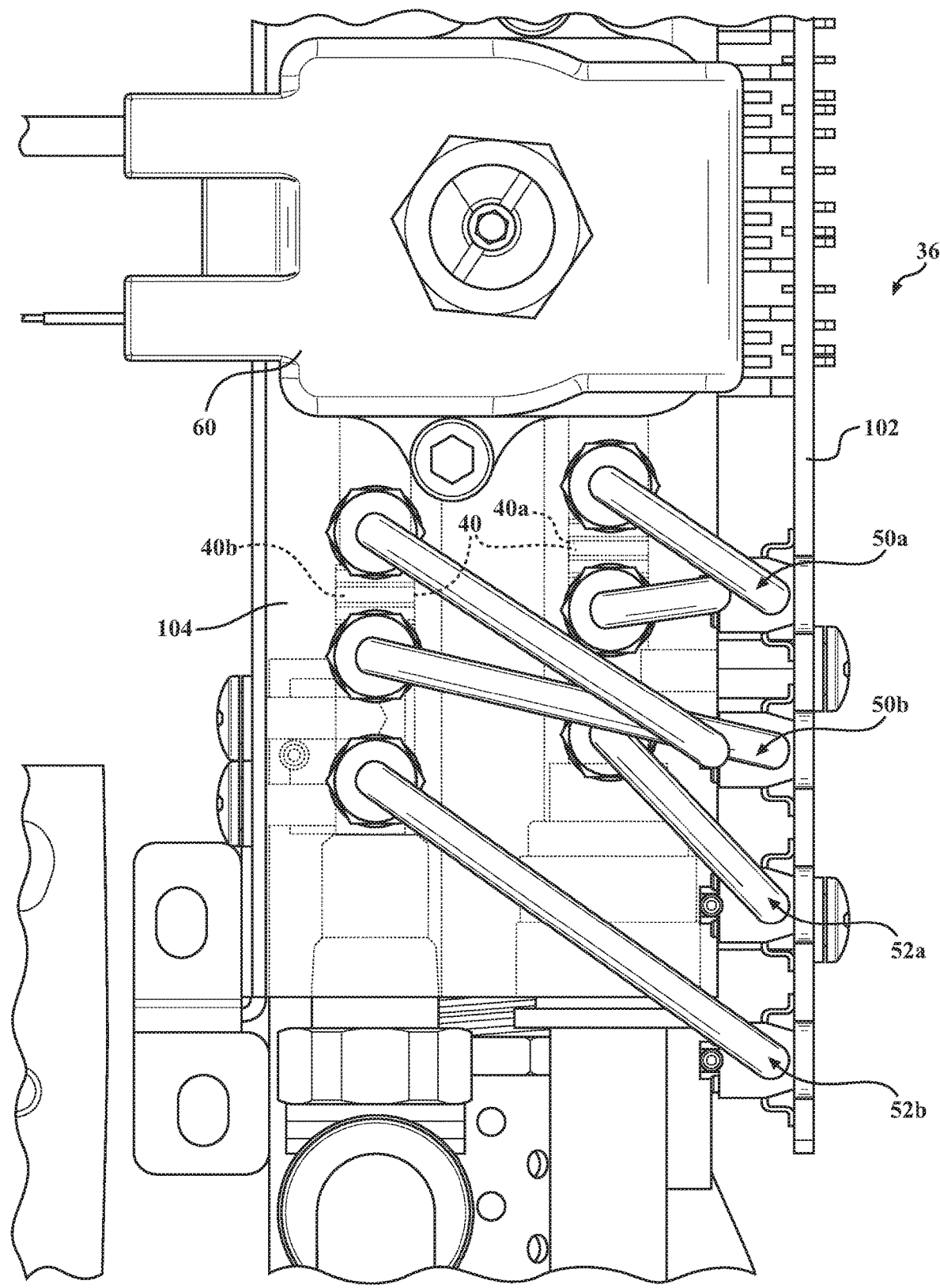
FIG. 8 is an overhead view of the aspiration manifold showing pressure sensors and their connections to the vacuum path.

FIGS. 7C and 8 provide alternative close-up views of the aspiration manifold 36. The aspiration manifold 36 includes the first sensor 48, the second sensor 57, the first vent valve 54, the second vent valve 60, and the printed circuit board 102. In this configuration, the first sensor 48, including the differential pressure sensor 50a and the gauge pressure sensor 52a, is available for use in determining the first vacuum pressure 180 in the surgical waste receiver 70 and generating a measured waste receiver pressure signal 132 based on the first vacuum pressure 180. Similarly, the second sensor 57, including the differential pressure sensor 50*b* and the gauge pressure sensor 52*b*, is available for use in determining a second vacuum pressure 182 at the surgical site and generating a measured tip pressure signal 133. Both of these signals are provided to the controller 102, which is a printed circuit board 102 in this configuration, to control the first vent valve 54 and the second vent valve 60.

The aspiration manifold 36 aids in distribution of air flow from the vacuum pump 74 to the vacuum path 40 and the pinch valve 62. Differential pressure sensors 50*a*, 50*b* may be used to monitor pressure or flow in the first portion 40*a* and second portion 40*b* of the vacuum path 40. Additionally, or alternatively, the gauge pressure sensors 52*a*, 52*b* may be used to monitor pressure in the first portion 40*a* and second portion 40*b*. A machined manifold 104, shown in FIGS. 7A-7C, distributes the vacuum flow in the first portion 40*a* and second portion 40*b* of the vacuum path 40 by manipulating vents to the atmosphere through the first vent valve 54 and second vent valve 60, as well as any other valves and mufflers.

A main muffler 106, shown in FIGS. 7A-7C, softens the pumping exhaust noise from the vacuum pump 74. The pulsing exhaust air is one of the largest noise contributors in the system 42. In this configuration, the mechanical actuator 100 has a large cross-sectional flow path to allow rapid venting of vacuum in the pinch valve 62 to the atmosphere. This allows the pinch valve 62 to quickly return to its open position.

Figure 9:
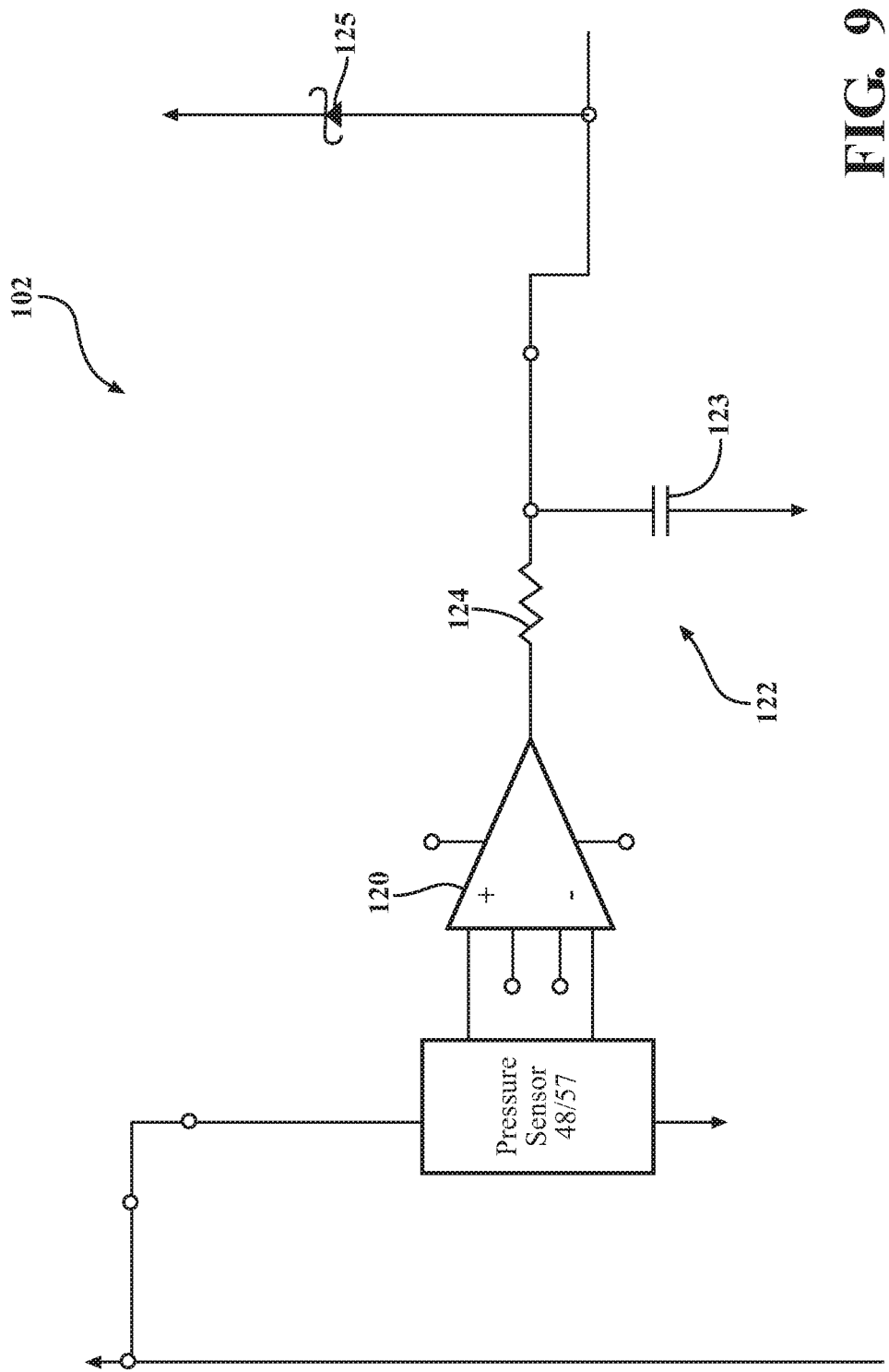
FIG. 9 is a circuit diagram for an exemplary pressure sensor.

FIG. 9 is a circuit diagram for an exemplary pressure sensor. In this example, a 15 PSI sensor is connected to the vacuum path 40. Measurements of the vacuum path 40 may be taken with the differential pressure sensors 50*a*. 50*b* and gauge pressure sensors 52*a*, 52*b*. The first and second sensors 48, 57 output a voltage representative of the pressure. The voltage signal is sent to an amplifier 120, in this configuration it is a differential operational amplifier with adjustable gain. The sensed signal is then passed through a low pass filter 122 to reduce noise from the signal. In this configuration, the low pass filter 122 comprises a capacitor 123 and a resistor 124. Finally, the signal is processed by a rectifier 125 to generate a modified signal. The modified signal is further processed in the controller 102. The processing of the sensed signal is depicted as using particular hardware but may also be accomplished with general purpose hardware and software.

II. Dual Regulation

To improve control responsiveness during aspiration, the console 20, or more particularly, the aspiration manifold 36 includes the first vent valve 54, the first sensor 48, the second vent valve 60, and the second sensor 57. As mentioned above, the first vent valve 54 may be associated with the clean side venting mechanism. The first vent valve 54 is positioned along the first portion 40*a* of the vacuum path, the second vent valve 60 is positioned at a terminal end 47 of the second portion 40*b* of the vacuum path 40 to regulate the aspiration system 42, or at a point proximal the fluid backflow device 462.

The console 20 may include a controller 102. The first and second sensors 48, 57 are coupled to the controller 102 to provide dual regulation of the system 42. The controller 102 is configured to control the first and second vent valves 54, 60 to regulate vacuum levels in the aspiration system 42. More specifically, the controller 102 is configured to independently control a position of the first vent valve 54 and a position of the second vent valve 60 based on the output of the first sensor 48 and the second sensor 57, respectively.

Adjustments to both the first vent valve 54 and the second vent valve 60 help to maintain the desired vacuum pressure at the surgical site. In this configuration, the first vent valve 54 and second vent valve 60 are variable flow iDP (intelligent diagnostic positioner) valves. The air flow through the first vent valve 54 and second vent valve 60 is proportional to current, which is controlled by a first PID (proportional integrated derivative) control loop 126 and a second PID control loop 128 in the controller 102. The first and second PID control loops 126, 128 are described further below.

The first sensor 48 is positioned along the first portion 40*a* of the vacuum path 40 to effectively sense pressure in the surgical waste receiver 70. Additionally, in order to provide faster, more responsive control, the second sensor 57 and the second vent valve 60 are included along the second portion 40*b* of the vacuum path 40.

In this configuration, the first sensor 48 may include the differential pressure sensor 50*a* and/or the gauge pressure sensor 52*a*. In an alternative configuration, different types of pressure sensors may be used. Readings from the first sensor 48 are used to generate a first input signal 232, which is sent to the controller 102 to control the first vent valve 54 to selectively open the first portion 40*a* of the vacuum path 40 to the atmosphere. The first input signal may be based on the first vacuum pressure 180. Additionally, or alternatively, the first input signal 232 may be the measured waste receiver pressure signal 132. In other configurations, the first input signal 232 may be based on a maximum first vent current 156 or a first vent current 164.

Based on the signals provided by the first sensor 48, the first vent valve 54 may be positioned to vent the vacuum path 40 to the atmosphere. This decreases vacuum pressure in the first portion 40*a* of the vacuum path 40 and ultimately the throughout the vacuum path 40 albeit at a slower response speed than the decrease in vacuum pressure at the tip 30 of the ultrasonic surgical handpiece 28 caused by the second vent valve 60 opening. The first vent valve 54 may be a variable valve that may be mechanically, electrically, or pneumatically actuated.

The combination of the first sensor 48 and the first vent valve 54 being positioned along the first portion 40*a* of the vacuum path 40 helps control the vacuum pressure at the surgical site. But the control provided by the first vent valve 54 may be slow to respond to changes in the pressure in the system 42 due to the large volume of the surgical waste receiver 70, the first portion 40*a* of the vacuum path 40, and the third portion 40*c* of the vacuum path 40. The compliance of the first portion 40*a* of the vacuum path 40 and the third portion 40*c* of the vacuum path 40 (the expansion contraction of the first portion 40*a* of the vacuum path 40 and the third portion 40*c* of the vacuum path 40) may exacerbate the problem. This is because the lines defining the portions 40*a*, 40*b*, and 40*c* of the vacuum path 40 may expand, resulting in an even larger volume as the pressure changes in the system 42.

To improve control responsiveness, the second sensor 57 and the second vent valve 60 are included along the second portion 40*b* of the vacuum path 40. Similar to the first sensor 48, the second sensor 57 may include the differential pressure sensor 50*b* and/or the gauge pressure sensor 52*b*. It will be appreciated that the first sensor 48 and the second sensor 57 may be any type of sensor including, but not limited to, a pressure sensor, temperature sensor, ultrasonic sensor, and gas sensor. It will be further appreciated that the first sensor 48 and the second sensor 57 may comprise any number of discrete sensors.

The second sensor 57 is configured to effectively sense the second vacuum pressure 182 at the surgical handpiece tip 30. Readings from the second sensor 57 are used to generate a second input signal 233, which is sent to the controller 102 to control the second vent valve 60 to selectively open the second portion 40b of the vacuum path 40 to the atmosphere.

The second vent valve 60 is operable to vent the vacuum path 40 to the atmosphere, decreasing the pressure in the vacuum path 40 or proximal a position of the fluid backflow device 462. More particularly, the second vent valve 60 is placed at the terminal end 47 of the second portion 40b of the vacuum path 40. In this configuration, the second vent valve 60 is also distal as compared to the second sensor 57. The second vent valve 60 may be the same as or different from the first vent valve 54.

In one configuration, or during certain modes, the vacuum pressure at the ultrasonic surgical handpiece 28 is wholly controlled by the second vent valve 60. In this configuration, the system 42 has lower pressures at the tip 30 of the ultrasonic surgical handpiece 28, which provides the feel of a lower aspiration setting, while the aspiration lines between the cassette 34 and the surgical waste receiver 70 clear at a faster rate, reducing clogs. Using the second sensor 57, the system 42 is able to monitor pressure at the tip 30 of the surgical handpiece 28, which allows the system 42 to detect possible clogs in the aspiration line. Readings from the second sensor 57 may be representation of pressure at the tip 30, which may be used to estimate a flow rate at the tip 30 of the surgical handpiece 28. Once a flow rate is estimated, the system 42 may detect possible clogs. Allowing the system 42 to detect potential clogs in the system 42 helps maintain ideal conditions during operation and optimizes the ultrasonic energy needed.

The second vacuum pressure 182 is less affected by the large volume of the surgical waste receiver 70, and thus, readings from the second sensor 57 are more representative of actual pressure at the tip 30 of the ultrasonic surgical handpiece 28, even though the second sensor 57 is also located in the console 20. Control of the second vent valve 60 provides a faster response for controlling pressure at the surgical handpiece tip 30 than control of the first vent valve 54. Faster control is achieved because there is far less volume between the surgical handpiece tip 30 and the second vent valve 60, than there is between the surgical waste receiver 70 and first portion 40a of the vacuum path 40 where the first vent valve 54 is located. This is also in large part because the second vent valve 60 is closer to the tip 30 of the ultrasonic surgical handpiece 28 relative to the surgical waste receiver 70, which contains a large volume. Additionally, because the second portion 40b of the vacuum path 40 contains far less volume than the first portion 40a of the vacuum path 40, the second portion 40b of the vacuum path 40 is less compliant and less likely to deform as a result of the vacuum pressure.

The vacuum control algorithm uses the signals representative of pressures at both the tip 30 and the surgical waste receiver 70 to dynamically adjust suction by modifying current supplied to the first vent valve 54 and second vent valve 69, and therefore changing pressure and flow in the system 42.

Figure 10:
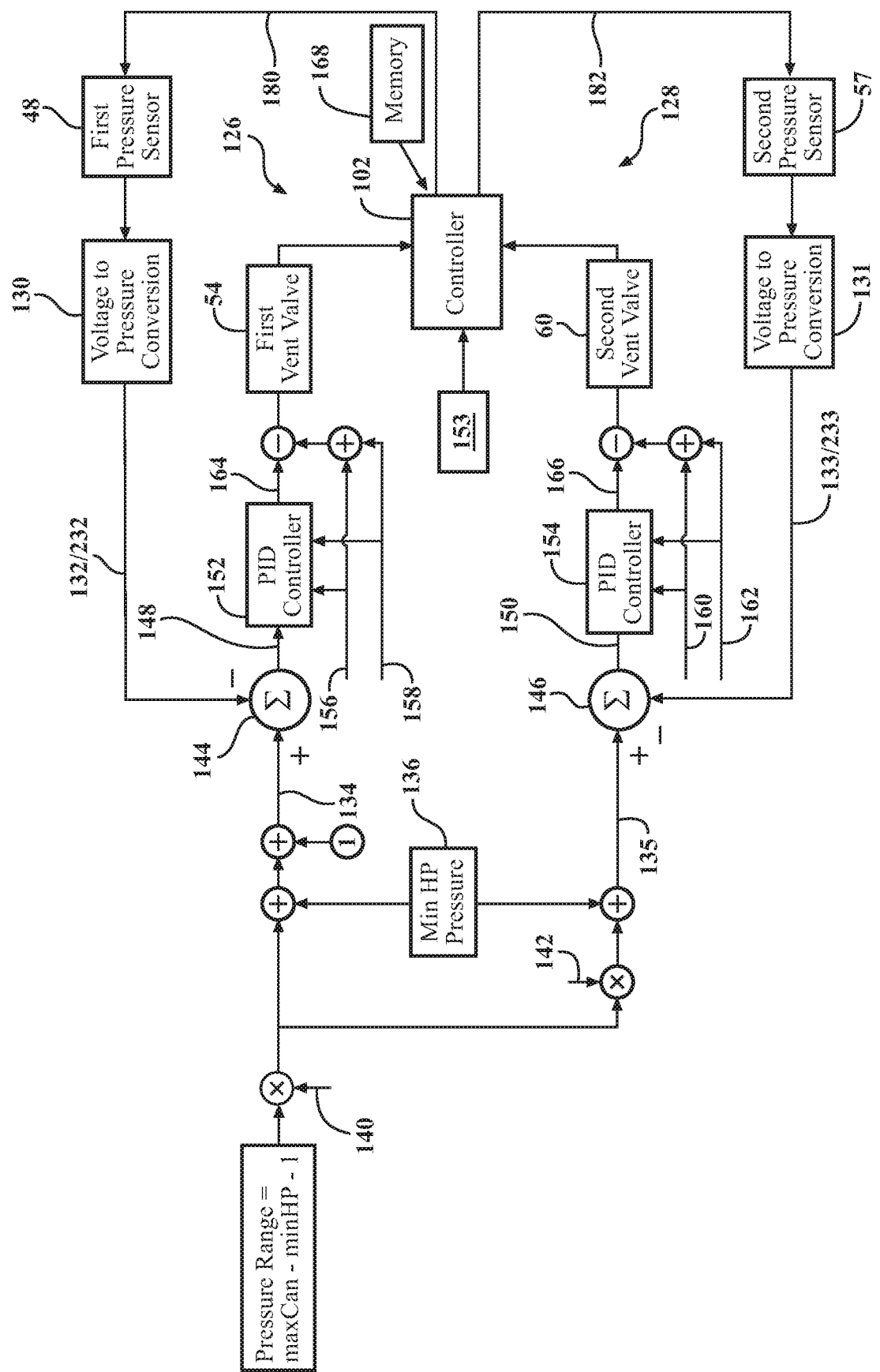
FIG. 10 is a block diagram of the control system, including a first PID control loop and a second PID control loop, used to adjust a first vent valve and a second vent valve for the aspiration system of FIG. 1.

FIG. 10 is a block diagram of a portion of the controller 102 showing the control system 42 used to control vacuum pressure in the ultrasonic surgical handpiece 28 to result in improved control responsiveness during operation of the ultrasonic surgical handpiece 28. The first and second PID control loops 126, 128 are used to adjust pressures in the vacuum path 40. A first and second PID controllers 152, 154 use a number of inputs to output the first vent current 164 and a second vent current 166, respectively, to adjust the position of the first and second vent valves 54, 60 respectively.

Signals from the first and second sensors 48, 57 provide the first and second input signals 232, 233. In one configuration, the first input signal 232 is the measured waste receiver pressure signal 132 and the second input signal 233 is the measured tip pressure signal 133. The other inputs may include the maximum waste receiver pressure signal 138, the minimum handpiece pressure signal 136, a tip clog signal, the aspiration setting 140, the foot pedal setting 142—all of which will be explained in greater detail below.

By reading in data from the first and second sensors 48, 57 and interfacing to the first and second vent valves 54, 60, the first and second PID control loops 126, 128 actively change current delivery to the first and second vent valves 54, 60 and improve system response. Further, in certain configurations wherein the first and second sensors are flowmeters, readings from the first and second sensors 48, 57 allow the controller 102 to monitor flow rates throughout the system 42 and to detect possible clogs in the aspiration line. Detection of clogs in the system 42 will be discussed in greater detail below.

The first PID control loop 126 receives input regarding the pressure in the first portion 40a of the vacuum path 40 and is therefore responsible for regulating a vacuum level that is maintained within the surgical waste receiver 70. This is needed to ensure that the pinch valve 62 can be actuated (as it is pneumatically controlled, and uses the pressure generated by the vacuum pump 74 to engage when needed) and to control the maximum amount of suction available in the aspiration system 42 at a given time. The time scale for the pressure control response in the first portion 40a of the vacuum path 40 is determined mainly by the pneumatic volume available within the surgical waste receiver 70.

Referring to FIG. 10, the first PID control loop 126 is implemented to control the first vent valve 54. In the first PID control loop 126, actual pressure readings are taken from the first sensor 48 coupled to the first portion 40a of the vacuum path 40. In this example, the first sensor 48 outputs a voltage based on measured pressure. This voltage may be converted to a pressure reading using a voltage to pressure conversion 130. The converted pressure signal is the measured waste receiver pressure signal 132.

A target waste receiver pressure signal 134 is determined based on parameters or information that may be stored in each surgical handpiece tip 30, the ultrasonic surgical handpiece 28, or the console 20, along with the power settings from the console 20. In this configuration, the target waste receiver pressure 134 is calculated from: the aspiration setting 140, the minimum handpiece pressure signal 136 and maximum waste receiver pressure signal 138. Once calculated, the target waste receiver pressure 134 is combined, with a first combiner 144, with the negative of the measured waste receiver pressure signal 132, and the difference between the two signals 134 and 132 is the waste receiver pressure error signal 148. In other configurations, the target waste receiver pressure 134 may be compared, combined, summed, or the like in relation with the measured waste receiver error signal 132 and the waste receiver pressure error signal 148. The waste receiver pressure error signal 148 is provided to the first PID controller 152.

The aspiration setting 140 and foot pedal setting 142 are both user selections input into the console 20.

In addition, the first PID controller 152 receives a signal indicating the maximum first vent current 156 and the minimum first vent current 158. Then, the first PID controller 152 outputs the first valve current 164 that will cause the first vent valve 54 to open or close. In this configuration, the first valve current 164 is inverted and a greater current will cause the first vent valve 54 to be more opened while a lower current will cause the first vent valve 54 to be more closed.

In one configuration, two parameters—the maximum waste receiver pressure 138 and minimum handpiece pressure 136—are stored in an RFID tag or other memory device associated with each surgical handpiece tip 30. Specifically, the RFID tag may be included in a sleeve associated with each surgical handpiece tip 30. Additionally, or alternatively, the controller 102 may include a memory device 168. It will be appreciated that the memory device associated with a surgical handpiece tip 30 may be the same or different memory device 168 associated with the controller 102. It will further be appreciated that the system 42 may include any number of memory devices.

Having maximum waste receiver pressure 138 and minimum handpiece pressure 136 stored in the surgical handpiece tip 30 or the sleeve associated with each tip provides a better system as many aspects of the system are changed depending on the surgical handpiece tip 30 used. The maximum pressure achievable in a system is dictated by the rate at which vacuum is vented. Each surgical handpiece tip 30 has different aspiration characteristics, and thus different steady state pressures when the first vent valve 54 and second vent valve 60 are fully opened and or fully closed. Each of the surgical handpiece tips 30 can be of different length, have different pre-aspiration hole configurations, have different sleeve sizes, and have different geometries all together. This leads to different absolute minimum and absolute maximum settings. In order to control over the full range available for each different tip the RFID tag or other memory device carries two parameters for use in the aspiration control system. The maximum waste receiver pressure 138 the control system will allow and the minimum tip pressure 136 the control system will allow. The maximum waste receiver pressure signal 138 is represented in FIG. 10 as a pressure range, which has already taken the maximum waste receiver pressure signal 138 into account.

The maximum waste receiver pressure signal 138 will usually be the highest pressure achievable with the first vent valve 54 and second vent valve 60 fully closed with no occlusion of the ultrasonic surgical handpiece tip 30. In some cases, the highest pressure achievable will be set higher than the maximum waste receiver pressure, if the tip is very open, and minimal pressure difference exists between the lowest aspiration case and the highest.

The minimum achievable steady state aspiration pressure is a measurement from the second sensor 57 taken from the second portion 40b of the vacuum path 40 with the first and second vent valves 54, 60 fully open, and the surgical handpiece tip 30 attached to the surgical handpiece 28 and console 20. This value is used to set the lowest possible vent side pressure setting. Without it, many of the lower settings in aspiration would be indistinguishable from one another. That is to say, the pressure set point would always sit under the measured pressure, causing the first and second vent valves 54, 60 to stay fully open, while never reaching the desired set point.

Referring back to FIG. 10, the second PID control loop 128 is used for fast control of suction pressure available at the ultrasonic surgical handpiece tip 30 through the second vent valve 60, allowing a consistent vacuum pressure, even under situations where aspiration load/occlusion is quickly varying. This is desirable for fine, precise and fast control of suction force available to the surgeon at the tip. The time scale for pressure changes at the tip is much quicker than that for the waste receiver and is constrained only by the volume of the tubing connecting the second sensor 57 to the surgical handpiece tip 30. This second PID control loop 128 operates with similar inputs and in the same fashion as the first PID control loop 126.

In the second PID control loop 128, actual pressure readings are taken from the second sensor 57, coupled to the second portion 40b of the vacuum path 40 or in communication with the dirty side flow path 460. In this example, the second sensor 57 outputs a voltage signal based on a measured pressure. This voltage signal may be converted to a pressure reading using a second voltage to pressure conversion 131. A measured tip pressure signal 133 is combined with a second combiner 146 with a target tip pressure signal 135. The target tip pressure signal 135 is determined based on parameters stored in a memory device associated with each surgical handpiece tip.

Additionally, or alternatively, the target tip pressure signal 135 may be based on a tip clog threshold. The tip clog threshold may be a parameter stored in the memory device associated with each surgical handpiece tip or the memory 168 associated with the controller 102. Once the tip clog threshold is determined, the system 42 may enter into a clog detection system using an operating routine 300 to determine if a clog is detected within the ultrasonic surgical handpiece 28. The operating routine 300 is described in greater detail further below.

The second PID control loop 128 calculates the target tip pressure 135 from the aspiration setting 140, the foot pedal setting 142, the minimum handpiece pressure signal 136 and maximum waste receiver pressure signal 138, the target tip pressure signal 135 is combined with the measured tip pressure signal 133 to generate a tip pressure error signal 150. It will be appreciated that the tip pressure error signal 150 is a tip error signal based on the tip pressure signal 133. In this configuration, the target tip pressure signal 135 is combined with the negative of the measured tip pressure signal 133 and the difference between the two signals is a handpiece pressure error signal 150. The tip pressure error signal 150 is provided to the second PID controller 154. In addition, the second PID controller 154 receives a signal indicating the maximum second vent current 160 and the minimum second vent current 162 for the second vent valve 60. The second PID controller 154 outputs the second vent current 166 that will cause the second vent valve 60 to open or close. In this configuration, the second vent current 166 is inverted, and a greater second vent current 166 will cause the second vent valve 60 to be more opened while a lower second valve current 166 will cause the second vent valve 60 to be more closed.

Positions of the first and second vent valves 54, 60 may be stored by the console 20 in the memory device 168. Alternatively, positions of the first and second vent valves 54, 60 may be based on a comparison, combination, evaluation, or a mathematical relationship between the measured waste receiver pressure signal 132 and the target waste receiver pressure signal 134, and the measured tip pressure signal 133 and the target tip pressure signal 135, respectively.

Figure 11:
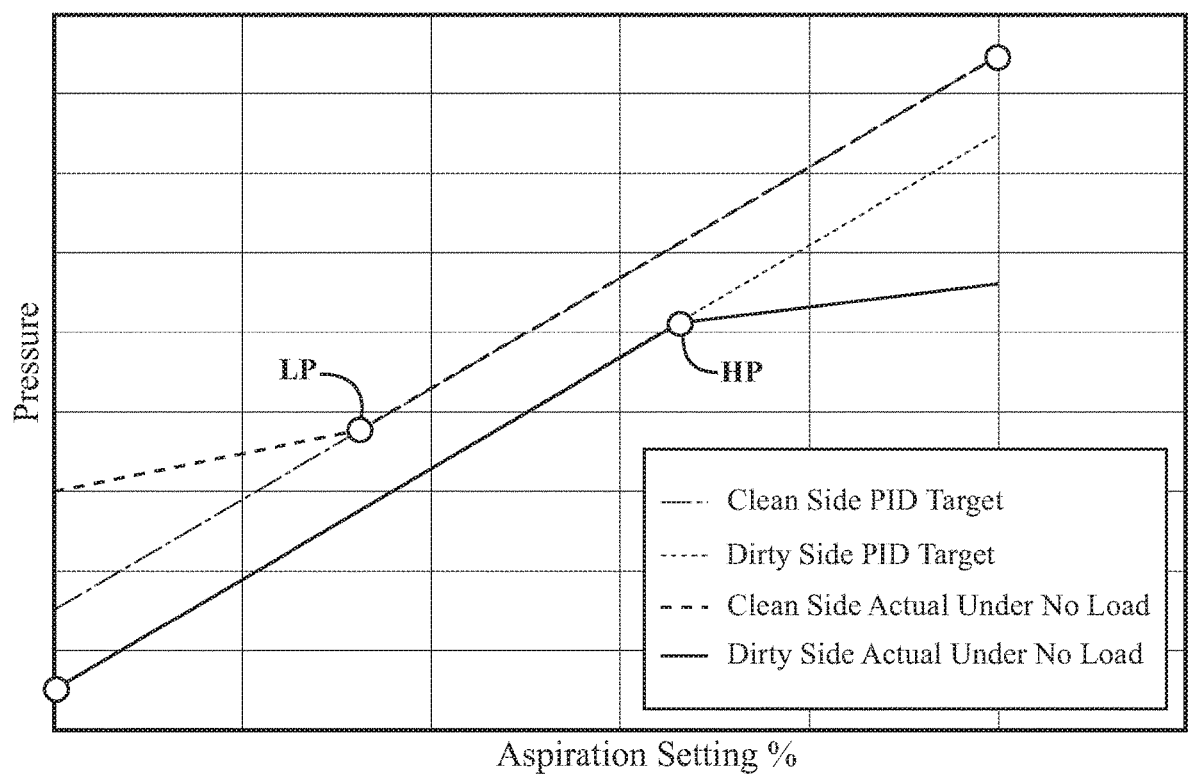
FIG. 11 is a graphical representation of target pressure and actual pressure at different points in the vacuum path based on different aspiration settings.

FIG. 11 shows an example of how the target pressure signals may be set and how those signals relate to the aspiration setting 140 and the minimum handpiece pressure signal 136 and the maximum waste receiver pressure signal 138. In addition to the minimum handpiece pressure 136 and maximum waste receiver pressure 138, there are two other points to consider in FIG. 11. There is a low point marked as LP on the lines displaying actual and target waste receiver pressure. While controlling at significantly low aspiration settings, there is a point LP at which the waste receiver pressure remains higher than the target waste receiver pressure 134 at all times. This means that the system 42 is wholly controlled by the second vent valve 60. In this scenario, the system 42 has lower pressures at the tip 30, which provides the feel of a lower aspiration setting, while the aspiration line between the cassette 34 and the surgical waster receiver 70 clears at a faster rate, reducing clogs.

At the higher end, at the point marked HP on the lines displaying actual and target handpiece pressure, the second vent valve 60 becomes completely closed, and is allowed to change to a higher pressure. This response is quick, as the main pneumatic volume of the surgical waste receiver 70 has already been sufficiently evacuated, and all that remains is the second portion 40b of the vacuum path 40 tubing itself. This allows for the higher settings to quickly achieve the desired higher pressures. Under load at the higher aspiration settings above this point, the pressure in the system 42 quickly matches the upper portion of the control target.

Figure 12:
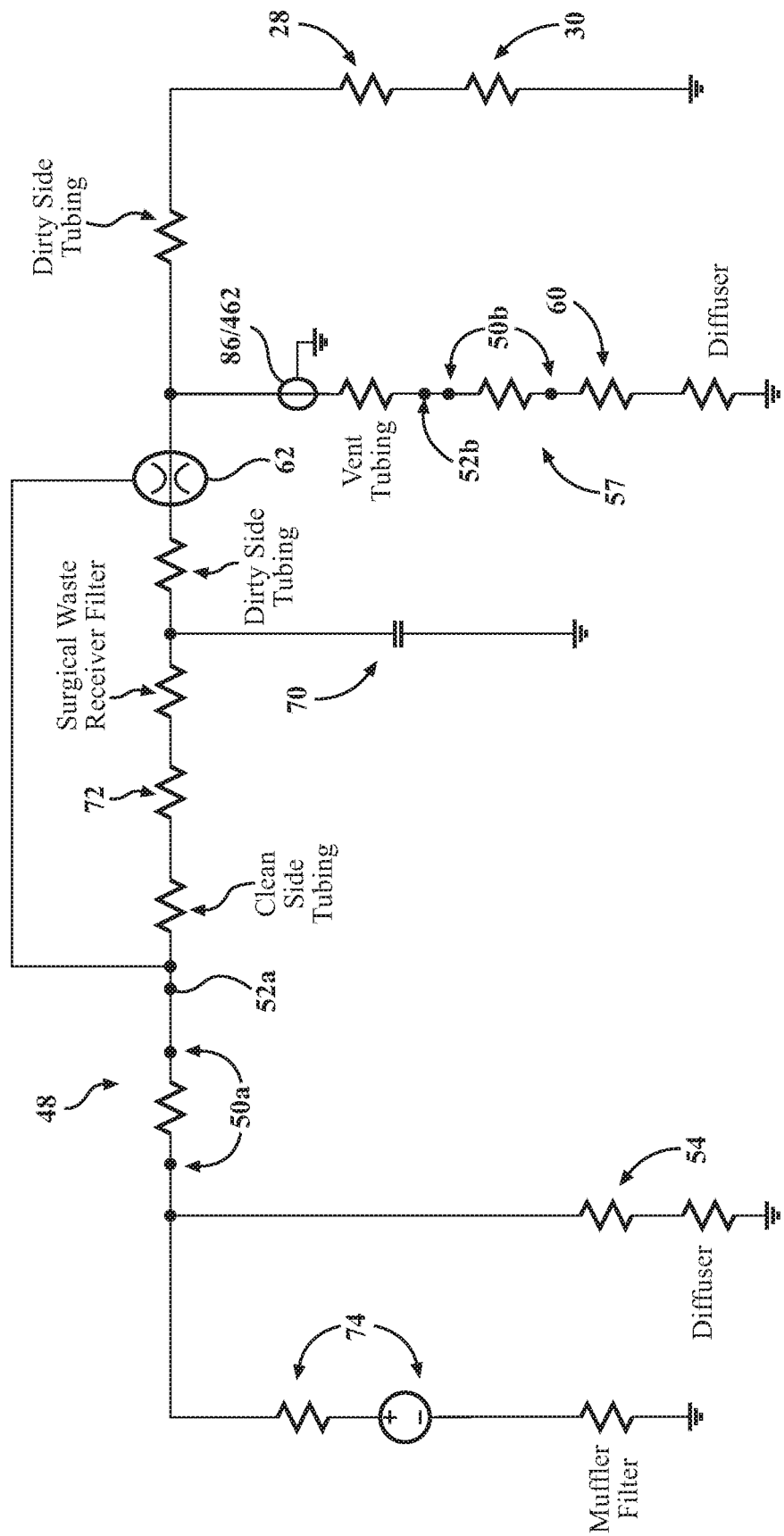
FIG. 12 depicts a schematic diagram of the aspiration system using electrical schematic connections to represent pneumatic resistances, according to one example.

Finally, as can be seen from the graph in FIG. 11 and the schematic in FIG. 12, the system 42 may be designed such that a higher pressure is maintained in the first portion 40a of the vacuum path 40 than the second portion 40b of the vacuum path 40. Additionally, or alternatively, a higher pressure is maintain on the "clean side" than the "dirty side" of the system 42 with the surgical waste receiver 70 providing a functional boundary between the two sides. In other words, a higher pressure is maintained from the surgical waste receiver 70 and filter 72 to the vacuum pump 74, while a lower pressure is maintained at the surgical handpiece tip 30 and in the remainder of the vacuum path 40. The pressure differential is maintained by the controller 102 controlling the first 54 and second vent valves 60. When the atmosphere enters the second portion 40b of the vacuum path 40 via the second vent valve 60, pressure is quickly lowered at the surgical handpiece tip 30.

FIG. 12 depicts a schematic diagram of the aspiration system using electrical schematic connections to represent pneumatic resistances. As shown, there are three components (a clean side tubing, filter 72, and a surgical waste receiver/canister tubing) between one side of the surgical waste receiver 70 and the pinch valve 62. On the other side, there is a dirty side tubing between the pinch valve 62 and the surgical waste receiver 70. On the "dirty side," two dirty side tubing and the ball valve 86/fluid backflow device 462 are provided. The second sensor 57 (including the differential sensor 50b and gauge sensor 52b), the second vent valve 60, and a diffuser are provided in communication with the ball valve 86/fluid backflow device 462. On the "clean side," the vacuum pump 74, the first sensor 48 (including the differential sensor 50a and gauge sensor 52a), the clean side tubing, the filter 72, and the surgical waste receiver/canister filter are provided. A muffler filter is provided in communication with the vacuum pump 74.

Due to the large volume in the surgical waste receiver 70 and pneumatic resistance of the system 42, a higher pressure may be maintained in the first portion 40a of the vacuum path 40 for a period of time, even though all portions of the vacuum path 40 are connected. The pressure differential helps ensure that surgical waste does not flow into the first portion 40a of the vacuum path 40, which is important as the tubes between the filter 72 and the vacuum pump 74 are not replaced between patients.

III. Clog Detection

Figure 13:
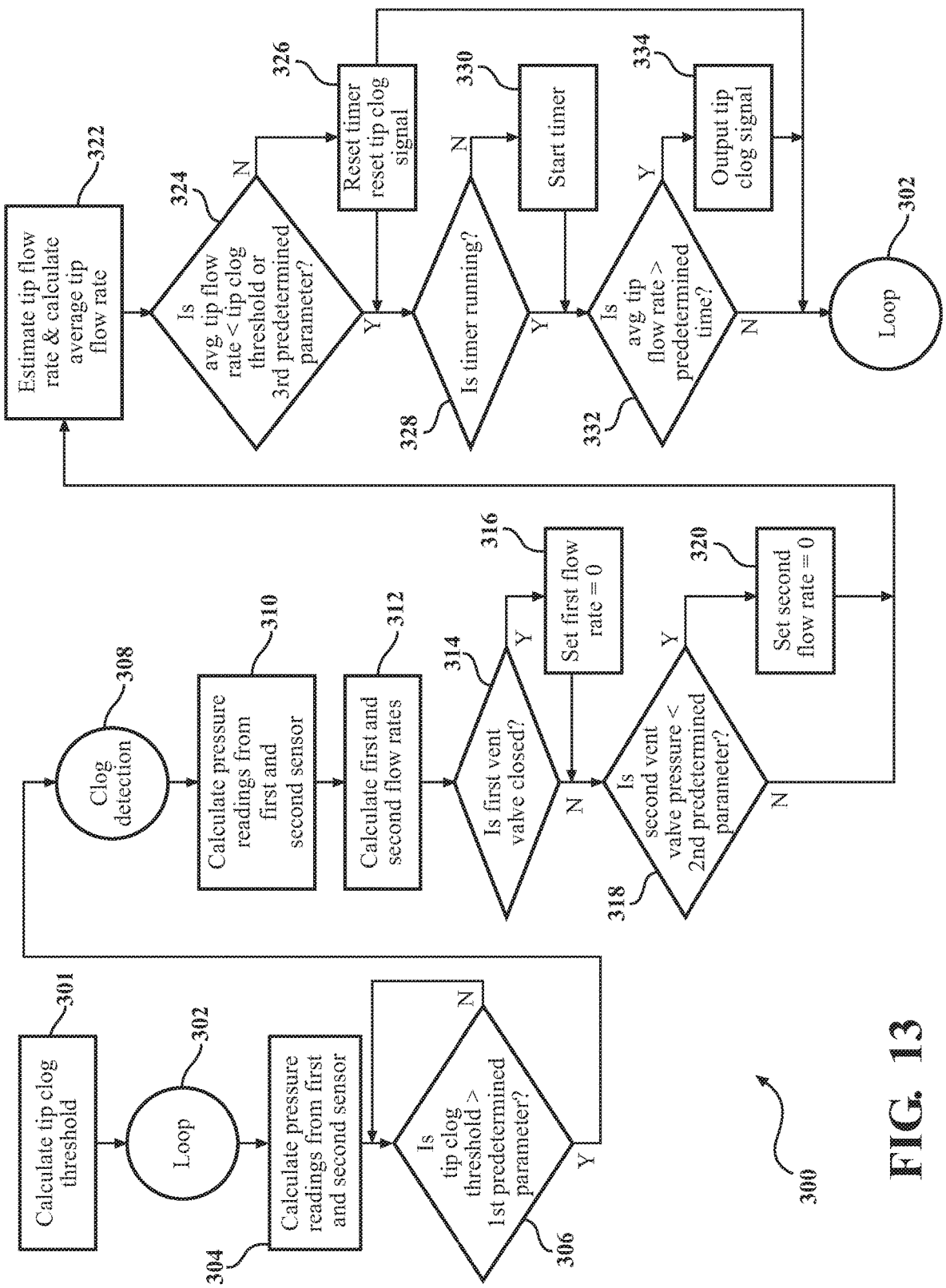
FIG. 13 depicts an operating routine implemented by the aspiration system to determine if a clog is detected within the ultrasonic surgical handpiece, according to one example.

During operation of the ultrasonic surgical handpiece 28, a common complication arises from a clog or occlusion of the ultrasonic surgical handpiece tip 30. While the tip 30 is clogged, the vacuum pump 74 continues and vacuum pressure builds up within the ultrasonic surgical handpiece 28. Eventually, there is break when the clog is cleared, resulting in a pressure drop thereby causing large quantity of surgical waste to be aspirated too quickly. This is known as a post-occlusion surge. Referring to FIG. 13, the system may implement an operating routine 300 that determines if a clog is detected within the surgical handpiece 28. The operating routine 300 is designed to reduce and/or prevent surges.

With readings from the first sensor 48 and the second sensor 57 and interfacing to the first vent valve 54 and second vent valve 60, respectively, the operating routine 300 goes through the following steps to determine if a clog is detected within the surgical handpiece 28. In one configuration, readings from the first and second sensor 48, 57 may be a first flow rate and a second flow rate, respectively.

Other advantages of the system 42 implementing the operating routine 300 include, but not limited to, maintaining ideal tissue resection rates, automatically adjusting aspiration to maintain an ideal flow rate for ultrasonic tissue resection, alerting user(s) of a potential clog, and automatically clearing clogs within the system.

Referring to FIG. 13 and referencing FIGS. 2 and 10, the operating routine 300 starts at step 301, where the tip clog threshold may be provided. In one configuration, once the system 42 is turned on and a tip of a surgical handpiece is attached, the tip clog threshold is calculated from a maximum pressure based on the maximum open loop response with no loading. In another configuration, the tip clog threshold may be a parameter stored in the memory device associated with each surgical handpiece tip such as the memory sleeve device located in a sleeve associated with the tip. The tip clog threshold may aid in determination of a possible clog.

At step 302, the system 42 enters into a clog control loop. At step 304, actual pressure readings are taken from the first sensor 48 and the second sensor 57. In one configuration, the first sensor 48 and the second sensor 57 may be the differential pressure sensor 50a and the differential pressure sensor 50b, respectively. In other configurations, the first sensor 48 and the second sensor 57 may be flow rate sensors.

Then, at step 306, using either the first or the second PID pressure control loops 126, 128, the readings from the first and second sensors 48, 57 may be compared to a first predetermined parameter. The first predetermined parameter may be stored in the memory device associated with the tip 30 or the memory device 168 of the controller 102. If the tip clog threshold is greater than the first predetermined parameter and the aspiration setting 140 is greater than a predetermined percentage limit, the operating routine 300 advances to step 308. The predetermined percentage limit may be a percentage stored in the memory device associated with the surgical handpiece tip 30 or the memory device 168 of the controller 102.

At step 308, the controller 102 may indicate that there is a possible clog detected within the surgical handpiece 28 and the operating routine 300 advances to step 310.

At step 310, the first and second vacuum pressure readings 180, 182 are taken from the first and second sensors 48, 57. More specifically, the differential pressure sensors 50a, 50b of the first and second sensors 48, 57 output the first and second input signal 232, 233 based on a change or drop in pressure within the first and second portion 40a, 40b of the vacuum path 40, respectively.

Then, at step 312, the first and the second flow rate are estimated based on pressure readings from the first and second sensor 48, 57, respectively. In one configuration, the controller 102 may estimate the first flow rate based on the input signal from the differential pressure sensor 50a. Similarly, the controller 102 may estimate the second flow rate based on the input signal from the differential pressure sensor 50b. Alternatively, in configurations where the first sensor 48 and the second sensor 57 are flowmeters, the controller 102 may determine the first and second flow rates, based on flow rate readings from the first and second sensors 48, 57.

In order to calibrate position of the first vent valve 54 to the first flow rate, the operating routine 300 may repeatedly evaluate the position of the first vent valve 54. At step 314, if the first vent valve 54 is closed, then the operating routine 300 advances to step 316 wherein the first flow rate is set to zero. If the first vent valve 54 is opened, then the operating routine 300 advances to step 318.

At step 318, the second vacuum pressure 182 is evaluated to calibrate the second flow rate. If the second vacuum pressure 182 at the second sensor 57 is less than a second predetermined parameter, then the operating routine 300 advances to step 320 wherein the second flow rate is set to zero. The second predetermined parameter may be a parameter stored in any of the aforementioned memory devices 168, 169. In one configuration, the second predetermined parameter is a unit of pressure expressed in pounds of force per square inch (PSI) of area. For example, the second predetermined parameter may be 0.005 PSI.

Once the first and second flow rates, are calibrated, at step 322, the controller 102 estimates a tip flow rate based on the second flow rate. Then, the controller 102 continuously evaluates the tip flow rate at a first predetermined time interval with input from a timer to determine an average tip flow rate. As previously mentioned, readings from the second sensor 57 are more representative of actual readings at the surgical handpiece tip 30, therefore the tip flow rate may be estimated from the second flow rate. The timer, as shown in FIG. 10, is coupled to the controller 102. The timer is operable to time a duration of the tip clog signal.

The average tip flow rate may be calculated from a rolling average of the tip flow rate. In other words, the controller 102 samples the tip flow rate for the first predetermined time interval and stores a certain number of tip flow rate readings in the rolling window. Once the certain number of tip flow rates have been included in the rolling window, the newest sample of tip flow rate replace the older sample prior to the latest average being calculated. For example, the first predetermined time interval is 3 seconds and the certain number is 5. Therefore, the rolling average is calculated over a sample of 5 tip flow rates every second with each tip flow rate being discarded every 3 seconds. It will be appreciated that the predetermined time interval may be stored in the memory device associated with the tip 30 of the ultrasonic surgical handpiece 28, the memory 168 associated with the controller 102, or any other memory.

At step 324, the average tip flow rate is compared to the tip clog threshold. If the average tip flow rate is less than the tip clog threshold, the operating routine 300 advances to step 328. If the average tip flow rate is greater than the tip clog threshold, the operating routine 300 advances to step 326 wherein the timer is reset or cleared and the tip clog signal is reset. In other words, the controller 102 has determined that there are no clogs within the surgical handpiece 28 and the operating routine 300 advances back to step 302.

In another configuration, the average tip flow rate may be compared to a third predetermined parameter. The third predetermined parameter may be a parameter stored in any of the aforementioned memory devices. Similar to the comparison with the tip clog threshold, if the average tip flow rate is greater than the third predetermined parameter, the timer and the tip clog signal are reset or cleared. The operating routine 300 advances back to step 302.

If the average tip flow rate is less than the tip clog threshold or the third predetermined parameter, the operating routine 300 advances to step 328. At step 328-330, if the timer is not running, then the timer is started or incremented from a zero time start value.

Using the timer, the operating routine 300 then evaluates the average tip flow rate for a second predetermined time interval at step 332. If the average tip flow rate is less than the tip clog threshold or the third predetermined parameter for longer than the second predetermined time interval, the controller 102 outputs the tip clog signal at step 334.

If the tip clog signal is outputted from the operating routine 300, the controller 102 indicates that there is a detection of a clog within the surgical handpiece 28 or at the tip of the surgical handpiece 28. Then, the user(s) and/or the controller may determine the next step to clear the clog and maintain ideal tissue resection rates. In one configuration, when the tip clog signal is outputted, the controller 102 may automatically adjust the positions of the first and second vent valve, control vacuum levels of the vacuum pump 74, adjust the aspiration setting, or any combinations thereof. For example, as shown in FIG. 10, the tip clog signal is one of the inputs into the second PID controller. The controller 102 may control the position of the second vent valve 60 based on the input of the tip clog signal.

Once the tip clog signal is outputted at step 334, the operating routine 300 then returns to step 302 wherein the operating routine 300 may return to the clog control loop. This enables the system 42 to automatically implement the operating routine 300 to detect possible clogs within the surgical handpiece 28.

It will be further appreciated that the terms "include," "includes," and "including" have the same meaning as the terms "comprise," "comprises," and "comprising."

For purposes of description herein, it is to be understood that the present disclosure may assume various alternative orientations, except where expressly specified to the contrary. It is also understood that the specific devices and processes illustrated in the attached drawings, and described in the following specification, are simply exemplary configurations of the inventive concepts defined herein. Hence, specific dimensions and other physical characteristics relating to the configurations disclosed herein are not be considered as limited, unless the claims expressly state otherwise.

Clauses:

i. An aspiration system to control vacuum pressure in an ultrasonic surgical handpiece to result in improved control responsiveness during aspiration, the system comprising:

a console for being fluidly coupled to the ultrasonic surgical handpiece, the console comprising a controller, a vacuum pump, a first sensor, a fluid backflow device, a second sensor, a clean side venting mechanism, and a second venting mechanism;

the controller configured to control the clean side venting mechanism based on an input signal from the first sensor; and the controller configured to control the second venting mechanism based on an input signal from the second sensor.

ii. An aspiration system to control vacuum pressure in an ultrasonic surgical handpiece to result in improved responsiveness during aspiration, the system comprising:

a console for being fluidly coupled to the ultrasonic surgical handpiece, the console comprising a controller, a vacuum pump, a first venting mechanism, and a second venting mechanism, said system configured to be placed in communication with a surgical waste receiver;

the controller configured to control the second venting mechanism in response to aspiration of liquid and solid material through the surgical handpiece and the controller is configured to control the first venting mechanism to maintain a desired pressure in the surgical waste receiver.

iii. An aspiration system to control vacuum pressure in an ultrasonic surgical handpiece, the system comprising:

a vacuum pump;

a joint defining a first joint port, a second joint port, and a third joint port, the first joint port for coupling a first flow path that extends from the ultrasonic surgical handpiece;

a second flow path coupled to the second joint port and coupled to a surgical waste receiver port;

a third flow path coupled to the third joint port;

a fourth flow path coupled to a second surgical waste receiver port;

a first sensor coupled to the fourth flow path and configured to provide a first signal;

a second sensor coupled to the third flow path and configured to provide a second signal; and a controller configured to output a tip clog signal based on the first signal and the second signal and control the vacuum pump based on the tip clog signal.

iv. An aspiration system to control vacuum pressure in an ultrasonic surgical handpiece, the system comprising:

a console including a vacuum pump;

a joint defining a first joint port, a second joint port, and a third joint port, the first joint port for coupling a first flow path that extends from the ultrasonic surgical handpiece;

a second flow path coupled to the second joint port and coupled to a surgical waste receiver port;

a third flow path coupled to the third joint port;

a fourth flow path coupled to a second surgical waste receiver port;

a first sensor coupled to the fourth flow path and configured to provide a first signal;

a second sensor coupled to the third flow path and configured provide a second signal;

a first vent valve coupled to the fourth flow path;

a second vent valve coupled to the third flow path; and a controller configured to determine a first flow rate based on the first signal and a second flow rate based on the second signal, output a tip clog signal based on the first signal and the second signal, and control a position of the first vent valve and/or a position of the second vent valve based on the tip clog signal.

v. A method for controlling vacuum pressure in an ultrasonic surgical handpiece, the method comprising:

driving a vacuum pump to create a vacuum pressure within an aspiration system;

determining a first flow rate of a dirty side flow path, the dirty side flow path positioned between the ultrasonic surgical handpiece and a fluid backflow device;

determining a second flow rate of a clean side flow path, the clean side flow path positioned between the vacuum pump and a surgical waste receiver;

outputting a tip clog signal based on an average tip flow rate based on the first flow rate and the second flow rate; and controlling the vacuum pump based on the tip clog signal.

vi. A fluid management system comprising:

a console defining a cassette aperture and having two pneumatic console ports therein;

a vacuum source connected to the console or integrated into the console and in communication with a first of the pneumatic console ports;

a first pressure sensor integrated into the console and in communication with a second of the pneumatic console ports;

a second pressure sensor integrated into the console and in communication with the first of the pneumatic console ports; and a cassette for selective slidable disposition within the cassette aperture and comprising:

a substantially rigid housing defining a chamber therein;

a liquid transfer portion of a pump including an intake side of the pump and an output side of the pump;

a plurality of fluid pathways disposed at least in part within the chamber, including:

a first fluid pathway including a first end connected with the intake side, and a second end for connecting with a supply fluid container;

a second fluid pathway including a first end connected with the output side, and a second end for connecting with a handpiece;

a third fluid pathway including a first end for connecting with the handpiece, and a second end for connecting with a waste container;

a fourth fluid pathway including a first end connected with a first console connector of the housing and a second end for connecting with the waste container, with the first console connector having a first pneumatic connector port pneumatically connected with the first of the pneumatic console ports when the cassette is installed in the cassette aperture; and a fifth fluid pathway having a first end connected with the third fluid pathway and a second end connected with a second console connector of the housing, with the second console connector having a second pneumatic connector port pneumatically connected with the second of the pneumatic console ports when the cassette is installed in the cassette aperture.

vii. A method of using a surgical irrigation cassette, comprising the steps of: providing the surgical irrigation cassette having each of:

a substantially rigid housing defining a chamber therein, a compressible peristaltic pump tube disposed outside of the housing, a plurality of fluid pathways disposed at least in part within the chamber, including:

a first fluid pathway including a first end connected with
a first end of the pump tube, and a second end for connecting with a supply fluid container, a second fluid pathway including a first end connected with a second end of the pump tube, and a second end for connecting with a handpiece, a third fluid pathway including a first end for connecting with the handpiece, and a second end for connecting with a waste container, a fourth fluid pathway including a first end connected with a first console connector fixed to the housing, and a second end for connecting with the waste container, and a fifth fluid pathway having a first end connected with the third fluid pathway, and a second end connected with a second console connector fixed to the housing;

inserting the cassette into a control console that includes or is connected to a vacuum source;

connecting the second end of the first fluid pathway to the supply fluid container;

connecting second end of the second fluid pathway to the handpiece;

connecting the first end of the third fluid pathway to the handpiece;

connecting the second end of the third fluid pathway to the waste container; and connecting the second end of the fourth fluid pathway to the waste container.

Several embodiments have been discussed in the foregoing description. However, the embodiments discussed herein are not intended to be exhaustive or limit the present disclosure to any particular form. The terminology, which has been used, is intended to be in the nature of words of description rather than of limitation. Many modifications and variations are possible in light of the above teachings and the present disclosure may be practiced otherwise than as specifically described.

The invention claimed is:

1. An aspiration system to control vacuum pressure in an ultrasonic surgical handpiece to result in improved control responsiveness during aspiration, the system comprising:
   a vacuum pump;
   a vacuum path that extends at least partially between a surgical handpiece connector and the vacuum pump, the vacuum path further including a joint wherein the joint divides the vacuum path into at least two flow paths;
   a first sensor coupled to a first portion of the vacuum path, the first portion of the vacuum path positioned between a surgical waste receiver connector and the vacuum pump, the first sensor configured to monitor a waste receiver pressure and provide a waste receiver pressure signal;
   a first vent valve coupled to the first portion of the vacuum path;
   a second vent valve coupled to a terminal end of a second portion of the vacuum path, the second portion of the vacuum path originating from the joint;
   a second sensor coupled to the second portion of the vacuum path and configured to monitor a vacuum pressure associated with a tip of the ultrasonic surgical handpiece and provide a tip pressure signal; and
   a controller configured to control a position of the first vent valve based on the waste receiver pressure signal and control a position of the second vent valve based on the tip pressure signal.

2. The aspiration system of claim 1, wherein the joint comprises a joint valve, operable to divide the vacuum path, having a first joint port, a second joint port and a third joint port, with the second portion of the vacuum path coupled to the third joint port.

3. The aspiration system of claim 2, wherein the joint valve is a ball valve that prevents surgical waste from passing into the second portion of the vacuum path.

4. The aspiration system of claim 2, wherein a third portion of the vacuum path is coupled to the second joint port and coupled to the surgical waste receiver connector.

5. The aspiration system of claim 1, further comprising a cassette for being fluidly coupled to the ultrasonic surgical handpiece, the cassette including an opening to a third portion of the vacuum path, and the opening aligning with a pinch valve that is operable to prevent vacuum pressure from reaching a tip of the ultrasonic surgical handpiece.

6. The aspiration system of claim 1, wherein the first portion of the vacuum path includes a clean side flow path and the second portion of the vacuum path includes a dirty side flow path.

7. The aspiration system of claim 1, wherein the first portion of the vacuum path has a volume greater than the second portion of the vacuum path.

8. The aspiration system of claim 1, wherein the first portion of the vacuum path has a compliance under pressure greater than the second portion of the vacuum path.

9. The aspiration system of claim 1, further comprising a pinch valve aligned with a third portion of the vacuum path, the third portion of the vacuum path extending from the joint to the surgical waste receiver connector, wherein the pinch valve is configured to prevent vacuum pressure from reaching the tip of the ultrasonic surgical handpiece when actuated.

10. The aspiration system of claim 9, further comprising a three-way valve coupled to the pinch valve, the three-way valve configured to couple the pinch valve to the atmosphere and/or to the first portion of the vacuum path.

11. The aspiration system of claim 9, wherein the pinch valve is configured to close when a foot pedal that operates the ultrasonic surgical handpiece is not depressed.

12. The aspiration system of claim 1, wherein the controller is further configured to control the position of the first vent valve to maintain a desired pressure in the surgical waste receiver.

13. The aspiration system of claim 1, wherein the controller further comprises a first PID control loop to control the first vent valve and a second PID control loop to control the second vent valve.

14. The aspiration system of claim 13, wherein the first PID control loop is configured to determine a waste receiver error signal based on the waste receiver pressure signal provided by the first sensor coupled to the first portion of the vacuum path and a target waste receiver pressure.

15. The aspiration system of claim 14, wherein the target waste receiver pressure is determined based on a parameter stored in a memory device associated with a tip of the ultrasonic surgical handpiece.

16. The aspiration system of claim 13, wherein the second PID control loop is configured to determine a tip error signal based on the tip pressure signal provided by the second sensor coupled to the second portion of the vacuum path and a target tip pressure.

17. The aspiration system of claim 16, wherein the target tip pressure is determined based on a parameter stored in a memory device associated with a tip of the ultrasonic surgical handpiece.

18. The aspiration system of claim 1, wherein the controller is configured to adjust the first vent valve and the second vent valve to maintain a higher pressure in the first portion of the vacuum path and a relatively lower pressure in the second portion of the vacuum path.

* * * * *